US007482321B2

(12) United States Patent
Glaesner et al.

(10) Patent No.: US 7,482,321 B2
(45) Date of Patent: Jan. 27, 2009

(54) EXTENDED GLUCAGON-LIKE PEPTIDE-1 ANALOGS

(75) Inventors: Wolfgang Glaesner, Indianapolis, IN (US); Wayne David Kohn, Indianapolis, IN (US); Rohn Lee Millican, Indianapolis, IN (US); Lianshan Zhang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 401 days.

(21) Appl. No.: 10/499,111

(22) PCT Filed: Jan. 3, 2003

(86) PCT No.: PCT/US03/00001

§ 371 (c)(1),
(2), (4) Date: Jun. 17, 2004

(87) PCT Pub. No.: WO03/058203

PCT Pub. Date: Jul. 17, 2003

(65) Prior Publication Data

US 2006/0014241 A1    Jan. 19, 2006

Related U.S. Application Data

(60) Provisional application No. 60/346,474, filed on Jan. 8, 2002, provisional application No. 60/405,097, filed on Aug. 21, 2002.

(51) Int. Cl.
*A61K 38/26* (2006.01)
*C07K 14/605* (2006.01)

(52) U.S. Cl. .......................................... 514/12; 530/308
(58) Field of Classification Search ...................... None
See application file for complete search history.

(56) References Cited

FOREIGN PATENT DOCUMENTS

| WO | WO 9943707 | 9/1999 |
|---|---|---|
| WO | WO 0007617 | 2/2000 |
| WO | WO 03/011892 | 2/2003 |

OTHER PUBLICATIONS

Perfetti et al., Eur. J. Endocr. 143, 717-725, 2000.*
Kieffer et al., Endocr. Rev. 20: 876-913, 1999.*
Adelhorst et al., J. Biol. Chem. 269: 6275-6278, 1994.*
Doyle, M. E., et al., "The Importance of the Nine-Amino Acid C-Terminal Sequence of Exendin-4 for Binding to the GLP-1 Receptor and for Biological Activity." Science Direct, vol. 114, Issues 2-3, Jul. 15, 2003, pp. 153-158.
Perry, T. A., et al., "The Glucagon-Like Peptides: A Double-Edged Therapeutic Sword?" Science Direct, vol. 24, Issue 7, Jul. 2003, pp. 377-383.

* cited by examiner

*Primary Examiner*—Robert Landsman
*Assistant Examiner*—Gyan Chandra
(74) *Attorney, Agent, or Firm*—Alejandro Martinez

(57) ABSTRACT

The invention encompasses GLP-1 peptides with modifications at various positions coupled with an extended C-terminus that provides increased stability.

16 Claims, No Drawings

SEQUENCE LISTING

<160> NUMBER OF SEQ ID NOS: 61

<210> SEQ ID NO 1
<211> LENGTH: 44
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine, or a Modified Residue
<220> FEATURE:
<221> NAME/KEY: MOD_RES
<222> LOCATION: (1)..(1)
<223> OTHER INFORMATION: Modified Residue at position 1 is desamino-histidine, 2-amino-histidine, beta-hydroxy-histidine, homohistidine, alpha-fluoromethyl-histidine, or alpha-methyl-histidine
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile, Ser, or Thr
<220> FEATURE:
<221> NAME/KEY: MISC_FEATURE
<222> LOCATION: (6)..(6)
<223> OTHER INFORMATION: Xaa at position 6 is Phe, Trp, or Tyr
<220> FEATURE:
<221> NAME/KEY: MISC_FEATURE
<222> LOCATION: (10)..(10)
<223> OTHER INFORMATION: Xaa at position 10 is Val, Trp, Ile, Leu,

```
        Phe, or Tyr
<220> FEATURE:
<221> NAME/KEY: MISC_FEATURE
<222> LOCATION: (12)..(12)
<223> OTHER INFORMATION: Xaa at position 12 is Ser, Trp, Tyr, Phe, Lys,
      Ile, Leu, or Val
<220> FEATURE:
<221> NAME/KEY: MISC_FEATURE
<222> LOCATION: (13)..(13)
<223> OTHER INFORMATION: Xaa at position 13 is Tyr, Trp, or Phe
<220> FEATURE:
<221> NAME/KEY: MISC_FEATURE
<222> LOCATION: (14)..(14)
<223> OTHER INFORMATION: Xaa at position 14 is Leu, Phe, Tyr, or Trp
<220> FEATURE:
<221> NAME/KEY: MISC_FEATURE
<222> LOCATION: (16)..(16)
<223> OTHER INFORMATION: Xaa at position 16 is Gly, Glu, Asp, or Lys
<220> FEATURE:
<221> NAME/KEY: MISC_FEATURE
<222> LOCATION: (19)..(19)
<223> OTHER INFORMATION: Xaa at position 19 is Ala, Val, Ile, or Leu
<220> FEATURE:
<221> NAME/KEY: MISC_FEATURE
<222> LOCATION: (21)..(21)
<223> OTHER INFORMATION: Xaa at position 21 is Glu, Ile, or Ala
<220> FEATURE:
<221> NAME/KEY: MISC_FEATURE
<222> LOCATION: (24)..(24)
<223> OTHER INFORMATION: Xaa at position 24 is Ala or Glu
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (28)..(28)
<223> OTHER INFORMATION: Xaa at position 28 is Lys, Asp, Arg, or Glu
<220> FEATURE:
<221> NAME/KEY: MISC_FEATURE
<222> LOCATION: (30)..(30)
<223> OTHER INFORMATION: Xaa at position 30 is Gly, Pro, or Arg
<220> FEATURE:
<221> NAME/KEY: MISC_FEATURE
<222> LOCATION: (31)..(31)
<223> OTHER INFORMATION: Xaa at position 31 is Gly, Pro, or Ser
<220> FEATURE:
<221> NAME/KEY: MISC_FEATURE
<222> LOCATION: (32)..(32)
<223> OTHER INFORMATION: Xaa at position 32 is Ser, Pro, or His
<220> FEATURE:
<221> NAME/KEY: MISC_FEATURE
<222> LOCATION: (33)..(33)
<223> OTHER INFORMATION: Xaa at position 33 is Ser, Arg, Thr, Trp, or
      Lys
<220> FEATURE:
<221> NAME/KEY: MISC_FEATURE
<222> LOCATION: (34)..(34)
<223> OTHER INFORMATION: Xaa at position 34 is Ser or Gly
<220> FEATURE:
<221> NAME/KEY: MISC_FEATURE
<222> LOCATION: (35)..(35)
<223> OTHER INFORMATION: Xaa at position 35 is Ala, Asp, Arg, Glu, Lys,
      Gly, or a modified residue.
<220> FEATURE:
<221> NAME/KEY: MOD_RES
<222> LOCATION: (35)..(35)
<223> OTHER INFORMATION: AMIDATION
<220> FEATURE:
<221> NAME/KEY: MISC_FEATURE
<222> LOCATION: (36)..(36)
<223> OTHER INFORMATION: Xaa at position 36 is Pro, Ala, absent or a
      modified residue.
<220> FEATURE:
<221> NAME/KEY: MOD_RES
<222> LOCATION: (36)..(36)
<223> OTHER INFORMATION: AMIDATION
<220> FEATURE:
<221> NAME/KEY: MISC_FEATURE
```

```
<222> LOCATION: (37)..(37)
<223> OTHER INFORMATION: Xaa is Pro, Ala, Absent, or a Modified Residue
<220> FEATURE:
<221>

```
<210> SEQ ID NO 2
<211> LENGTH: 41
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-histidine, D-histidine, or a Modified
      Residue
<220> FEATURE:
<221> NAME/KEY: MOD_RES
<222> LOCATION: (1)..(1)
<223> OTHER INFORMATION: Modified Residue at position 1 is
      desamino-histidine, 2-amino-histidine, beta-hydroxy-histidine,
      homohistidine, alpha-fluoromethyl-histidine, or
      alpha-methyl-histidine
<220> FEATURE:
<221> NAME/KEY: MISC_FEATURE
<222> LOCATION: (2)..(2)
<223> OTHER INFORMATION: Xaa is Ala, Gly, Val, Leu, Ile, Ser, or Thr
<220> FEATURE:
<221> NAME/KEY: MISC_FEATURE
<222> LOCATION: (6)..(6)
<223> OTHER INFORMATION: Xaa is Phe, Trp, or Tyr
<220> FEATURE:
<221> NAME/KEY: MISC_FEATURE
<222> LOCATION: (10)..(10)
<223> OTHER INFORMATION: Xaa is Val, Trp, Ile, Leu, Phe, or Tyr
<220> FEATURE:
<221> NAME/KEY: MISC_FEATURE
<222> LOCATION: (12)..(12)
<223> OTHER INFORMATION: Xaa is Ser, Trp, Tyr, Phe, Lys, Ile, Leu, or
      Val
<220> FEATURE:
<221> NAME/KEY: MISC_FEATURE
<222> LOCATION: (13)..(13)
<223> OTHER INFORMATION: Xaa is Tyr, Trp, or Phe
<220> FEATURE:
<221> NAME/KEY: MISC_FEATURE
<222> LOCATION: (14)..(14)
<223> OTHER INFORMATION: Xaa is Leu, Phe, Tyr, or Trp
<220> FEATURE:
<221> NAME/KEY: MISC_FEATURE
<222> LOCATION: (16)..(16)
<223> OTHER INFORMATION: Xaa is Gly, Glu, Asp, or Lys
<220> FEATURE:
<221> NAME/KEY: MISC_FEATURE
<222> LOCATION: (19)..(19)
<223> OTHER INFORMATION: Xaa is Ala, Val, Ile, or Leu
<220> FEATURE:
<221> NAME/KEY: MISC_FEATURE
<222> LOCATION: (21)..(21)
<223> OTHER INFORMATION: Xaa is Glu, Ile, or Ala
<220> FEATURE:
<221> NAME/KEY: MISC_FEATURE
<222> LOCATION: (24)..(24)
<223> OTHER INFORMATION: Xaa is Ala or Glu
<220> FEATURE:
<221> NAME/KEY: MISC_FEATURE
<222> LOCATION: (27)..(27)
<223> OTHER INFORMATION: Xaa is Val or Ile
<220> FEATURE:
<221> NAME/KEY: MISC_FEATURE
<222> LOCATION: (28)..(28)
<223> OTHER INFORMATION: Xaa is Lys, Asp, Arg, or Glu
<220> FEATURE:
<221> NAME/KEY: MISC_FEATURE
<222> LOCATION: (30)..(30)
<223> OTHER INFORMATION: Xaa is Gly, Pro, or Arg
<220> FEATURE:
<221> NAME/KEY: MISC_FEATURE
<222> LOCATION: (31)..(31)
<223> OTHER INFORMATION: Xaa is Gly, Pro, or Ser
<220> FEATURE:
<221> NAME/KEY: MISC_FEATURE
<222> LOCATION: (32)..(32)
<223> OTHER INFORMATION: Xaa is Ser, Pro, or His
```

```
<220> FEATURE:
<221> NAME/KEY: MISC_FEATURE
<222> LOCATION: (33)..(33)
<223> OTHER INFORMATION: Xaa is Ser, Arg, Thr, Trp, or Lys
<220> FEATURE:
<221> NAME/KEY: MISC_FEATURE
<222> LOCATION: (34)..(34)
<223> OTHER INFORMATION: Xaa is Ser or Gly
<220> FEATURE:
<221> NAME/KEY: MISC_FEATURE
<222> LOCATION: (35)..(35)
<223> OTHER INFORMATION: Xaa is Ala, Asp, Arg, Glu, Lys, Gly, or a
      Modified Residue
<220> FEATURE:
<221> NAME/KEY: MOD_RES
<222> LOCATION: (35)..(35)
<223> OTHER INFORMATION: AMIDATION
<220> FEATURE:
<221> NAME/KEY: MISC_FEATURE
<222> LOCATION: (36)..(36)
<223> OTHER INFORMATION: Xaa is Pro, Ala, Absent, or a Modified Residue
<220> FEATURE:
<221> NAME/KEY: MOD_RES
<222> LOCATION: (36)..(36)
<223> OTHER INFORMATION: AMIDATION
<220> FEATURE:
<221> NAME/KEY: MISC_FEATURE
<222> LOCATION: (37)..(37)
<223> OTHER INFORMATION: Xaa is Pro, Ala, Absent or a Modified Residue
<220> FEATURE:
<221> NAME/KEY: MOD_RES
<222> LOCATION: (37)..(37)
<223> OTHER INFORMATION: AMIDATION
<220> FEATURE:
<221> NAME/KEY: MISC_FEATURE
<222> LOCATION: (38)..(38)
<223> OTHER INFORMATION: Xaa is Pro, Ala, Arg, Lys, His, Absent or a
      Modified Residue
<220> FEATURE:
<221> NAME/KEY: MOD_RES
<222> LOCATION: (38)..(38)
<223> OTHER INFORMATION: AMIDATION
<220> FEATURE:
<221> NAME/KEY: MISC_FEATURE
<222> LOCATION: (39)..(39)
<223> OTHER INFORMATION: Xaa is Ser, His, Pro, Lys, Arg, Absent or a
      Modified Residue
<220> FEATURE:
<221> NAME/KEY: MOD_RES
<222> LOCATION: (39)..(39)
<223> OTHER INFORMATION: AMIDATION
<220> FEATURE:
<221> NAME/KEY: MISC_FEATURE
<222> LOCATION: (40)..(40)
<223> OTHER INFORMATION: Xaa is His, Ser, Arg, Lys, Absent or a
      Modified Residue
<220> FEATURE:
<221> NAME/KEY: MOD_RES
<222> LOCATION: (40)..(40)
<223> OTHER INFORMATION: AMIDATION
<220> FEATURE:
<221> NAME/KEY: MISC_FEATURE
<222> LOCATION: (41)..(41)
<223> OTHER INFORMATION: Xaa is His, Ser, Arg, Lys, Absent or a Modified
      Residue
<220> FEATURE:
<221> NAME/KEY: MOD_RES
<222> LOCATION: (41)..(41)
<223> OTHER INFORMATION: AMIDATION

<400> SEQUENCE: 2

Xaa Xaa Glu Gly Thr Xaa Thr Ser Asp Xaa Ser Xaa Xaa Xaa Glu Xaa
1               5                   10                  15

Gln Ala Xaa Lys Xaa Phe Ile Xaa Trp Leu Xaa Xaa Gly Xaa Xaa Xaa
            20                  25                  30

Xaa Xaa Xaa Xaa Xaa Xaa Xaa Xaa Xaa
```

```
<210> SEQ ID NO 3
<211> LENGTH: 41
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-histidine, D-histidine, or a Modified
      Residue
<220> FEATURE:
<221> NAME/KEY: MOD_RES
<222> LOCATION: (1)..(1)
<223> OTHER INFORMATION: Modified Residue at position 1 is
      desamino-histidine,
      2-amino-histidine, beta-hydroxy-histidine, homohistidine,
      alpha-fluoromethyl-histidine, or alpha-methyl-histidine
<220> FEATURE:
<221> NAME/KEY: MISC_FEATURE
<222> LOCATION: (2)..(2)
<223> OTHER INFORMATION: Xaa is Gly, Val, Leu, Ile, Ser, or Thr
<220> FEATURE:
<221> NAME/KEY: MISC_FEATURE
<222> LOCATION: (10)..(10)
<223> OTHER INFORMATION: Xaa is Val, Trp, Ile, Leu, Phe, or Tyr
<220> FEATURE:
<221> NAME/KEY: MISC_FEATURE
<222> LOCATION: (16)..(16)
<223> OTHER INFORMATION: Xaa is Gly, Glu, Asp, or Lys
<220> FEATURE:
<221> NAME/KEY: MISC_FEATURE
<222> LOCATION: (19)..(19)
<223> OTHER INFORMATION: Xaa is Ala, Val, Ile, or Leu
<220> FEATURE:
<221> NAME/KEY: MISC_FEATURE
<222> LOCATION: (27)..(27)
<223> OTHER INFORMATION: Xaa is Val or Ile
<220> FEATURE:
<221> NAME/KEY: MISC_FEATURE
<222> LOCATION: (28)..(28)
<223> OTHER INFORMATION: Xaa is Lys, Asp, Arg, or Glu
<220> FEATURE:
<221> NAME/KEY: MISC_FEATURE
<222> LOCATION: (30)..(30)
<223> OTHER INFORMATION: Xaa is Gly, Pro, or Arg
<220> FEATURE:
<221> NAME/KEY: MISC_FEATURE
<222> LOCATION: (31)..(31)
<223> OTHER INFORMATION: Xaa is Gly, Pro, or Ser
<220> FEATURE:
<221> NAME/KEY: MISC_FEATURE
<222> LOCATION: (32)..(32)
<223> OTHER INFORMATION: Xaa is Ser, Pro, or His
<220> FEATURE:
<221> NAME/KEY: MISC_FEATURE
<222> LOCATION: (33)..(33)
<223> OTHER INFORMATION: Xaa is Ser, Arg, Thr, Trp, or Lys
<220> FEATURE:
<221> NAME/KEY: MISC_FEATURE
<222> LOCATION: (34)..(34)
<223> OTHER INFORMATION: Xaa is Ser or Gly
<220> FEATURE:
<221> NAME/KEY: MISC_FEATURE
<222> LOCATION: (35)..(35)
<223> OTHER INFORMATION: Xaa is Ala, Asp, Arg, Glu, Lys, or Gly
<220> FEATURE:
<221> NAME/KEY: MISC_FEATURE
<222> LOCATION: (36)..(36)
<223> OTHER INFORMATION: Xaa is Pro or Ala
<220> FEATURE:
<221> NAME/KEY: MISC_FEATURE
<222> LOCATION: (37)..(37)
<223> OTHER INFORMATION: Xaa is Pro, Ala, or a Modified Residue
<220> FEATURE:
<221> NAME/KEY: MOD_RES
```

```
<222> LOCATION: (37)..(37)
<223> OTHER INFORMATION: AMIDATION
<220> FEATURE:
<221> NAME/KEY: MISC_FEATURE
<222> LOCATION: (38)..(38)
<223> OTHER INFORMATION: Xaa is Pro, Ala, Arg, Lys, His, Absent or a
      Modified Residue
<220> FEATURE:
<221> NAME/KEY: MOD_RES
<222> LOCATION: (38)..(38)
<223> OTHER INFORMATION: AMIDATION
<220> FEATURE:
<221> NAME/KEY: MISC_FEATURE
<222> LOCATION: (39)..(39)
<223> OTHER INFORMATION: Xaa is Ser, His, Pro, Lys, Arg, Absent or a
      Modified Residue
<220> FEATURE:
<221> NAME/KEY: MOD_RES
<222> LOCATION: (39)..(39)
<223> OTHER INFORMATION: AMIDATION
<220> FEATURE:
<221> NAME/KEY: MISC_FEATURE
<222> LOCATION: (40)..(40)
<223> OTHER INFORMATION: Xaa is His, Ser, Arg, Lys, Absent or a Modified
      Residue
<220> FEATURE:
<221> NAME/KEY: MOD_RES
<222> LOCATION: (40)..(40)
<223> OTHER INFORMATION: AMIDATION
<220> FEATURE:
<221> NAME/KEY: MISC_FEATURE
<222> LOCATION: (41)..(41)
<223> OTHER INFORMATION: Xaa is His, Ser, Arg, Lys, Absent or a Modified
      Residue
<220> FEATURE:
<221> NAME/KEY: MOD_RES
<222> LOCATION: (41)..(41)
<223> OTHER INFORMATION: AMIDATION

<400> SEQUENCE: 3

Xaa Xaa Glu Gly Thr Phe Thr Ser Asp Xaa Ser Ser Tyr Lys Glu Xaa
1               5                   10                  15

Gln Ala Xaa Lys Glu Phe Ile Ala Trp Leu Xaa Xaa Gly Xaa Xaa Xaa
            20                  25                  30

Xaa Xaa Xaa Xaa Xaa Xaa Xaa Xaa Xaa
        35                  40

<210> SEQ ID NO 4
<211> LENGTH: 41
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-histidine, D-histidine, or a Modified
      Residue
<220> FEATURE:
<221> NAME/KEY: MOD_RES
<222> LOCATION: (1)..(1)
<223> OTHER INFORMATION: Modified Residue at position 1 is
      desamino-histidine,
      2-amino-histidine, beta-hydroxy-histidine, homohistidine,
      alpha-fluoromethyl-histidine, or alpha-methyl-histidine
<220> FEATURE:
<221> NAME/KEY: MISC_FEATURE
<222> LOCATION: (2)..(2)
<223> OTHER INFORMATION: Xaa is Gly, Val, Leu, Ile, Ser, or Thr
<220> FEATURE:
<221> NAME/KEY: MISC_FEATURE
<222> LOCATION: (16)..(16)
<223> OTHER INFORMATION: Xaa is Gly, Glu, Asp, or Lys
<220> FEATURE:
<221> NAME/KEY: MISC_FEATURE
```

```
<222> LOCATION: (19)..(19)
<223> OTHER INFORMATION: Xaa is Ala, Val, Ile, or Leu
<220> FEATURE:
<221> NAME/KEY: MISC_FEATURE
<222> LOCATION: (27)..(27)
<223> OTHER INFORMATION: Xaa is Val or Ile
<220> FEATURE:
<221> NAME/KEY: MISC_FEATURE
<222> LOCATION: (32)..(32)
<223> OTHER INFORMATION: Xaa is Ser, Pro, or His
<220> FEATURE:
<221> NAME/KEY: MISC_FEATURE
<222> LOCATION: (33)..(33)
<223> OTHER INFORMATION: Xaa is Ser, Arg, Thr, Trp, or Lys
<220> FEATURE:
<221> NAME/KEY: MISC_FEATURE
<222> LOCATION: (34)..(34)
<223> OTHER INFORMATION: Xaa is Ser or Gly
<220> FEATURE:
<221> NAME/KEY: MISC_FEATURE
<222> LOCATION: (35)..(35)
<223> OTHER INFORMATION: Xaa is Ala, Asp, Arg, Glu, Lys, or Gly
<220> FEATURE:
<221> NAME/KEY: MISC_FEATURE
<222> LOCATION: (36)..(36)
<223> OTHER INFORMATION: Xaa is Pro or Ala
<220> FEATURE:
<221> NAME/KEY: MISC_FEATURE
<222> LOCATION: (37)..(37)
<223> OTHER INFORMATION: Xaa is Pro, Ala, or a Modified Residue
<220> FEATURE:
<221> NAME/KEY: MOD_RES
<222> LOCATION: (37)..(37)
<223> OTHER INFORMATION: AMIDATION
<220> FEATURE:
<221> NAME/KEY: MISC_FEATURE
<222> LOCATION: (38)..(38)
<223> OTHER INFORMATION: Xaa is Pro, Ala, Arg, Lys, His, Absent or a
     Modified Residue
<220> FEATURE:
<221> NAME/KEY: MOD_RES
<222> LOCATION: (38)..(38)
<223> OTHER INFORMATION: AMIDATION
<220> FEATURE:
<221> NAME/KEY: MISC_FEATURE
<222> LOCATION: (39)..(39)
<223> OTHER INFORMATION: Xaa is Ser, His, Pro, Lys, Arg, Absent or a
     Modified Residue
<220> FEATURE:
<221> NAME/KEY: MOD_RES
<222> LOCATION: (39)..(39)
<223> OTHER INFORMATION: AMIDATION
<220> FEATURE:
<221> NAME/KEY: MISC_FEATURE
<222> LOCATION: (40)..(40)
<223> OTHER INFORMATION: Xaa is His, Ser, Arg, Lys, Absent or a
     Modified Residue
<220> FEATURE:
<221> NAME/KEY: MOD_RES
<222> LOCATION: (40)..(40)
<223> OTHER INFORMATION: AMIDATION
<220> FEATURE:
<221> NAME/KEY: MISC_FEATURE
<222> LOCATION: (41)..(41)
<223> OTHER INFORMATION: Xaa His, Ser, Arg, Lys, Absent or a Modified
     Residue
<220> FEATURE:
<221> NAME/KEY: MOD_RES
<222> LOCATION: (41)..(41)
<223> OTHER INFORMATION: AMIDATION

<400> SEQUENCE: 4

Xaa Xaa Glu Gly Thr Phe Thr Ser Asp Val Ser Ser Tyr Lys Glu Xaa
1               5                   10                  15

Gln Ala Xaa Lys Glu Phe Ile Ala Trp Leu Xaa Lys Gly Gly Pro Xaa
            20                  25                  30
```

```
Xaa Xaa Xaa Xaa Xaa Xaa Xaa Xaa
        35                  40

<210> SEQ ID NO 5
<211> LENGTH: 31
<212> TYPE: PRT
<213> ORGANISM: Homo sapiens

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 6
<211> LENGTH: 31
<212> TYPE: PRT
<213> ORGANISM: Artificial
<220> FEATURE:
<223> OTHER INFORMATION: synthetic construct

<400> SEQUENCE: 6

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 7
<211> LENGTH: 39
<212> TYPE: PRT
<213> ORGANISM: Artificial
<220> FEATURE:
<223> OTHER INFORMATION: synthetic construct
<220> FEATURE:
<221> NAME/KEY: MOD_RES
<222> LOCATION: (39)..(39)
<223> OTHER INFORMATION: Ser at position 39 is amidated

<400> SEQUENCE: 7

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Asp Gly Gly Pro Ser
            20                  25                  30

Ser Gly Arg Pro Pro Pro Ser
        35

<210> SEQ ID NO 8
<211> LENGTH: 39
<212> TYPE: PRT
<213> ORGANISM: Artificial
<220> FEATURE:
<223> OTHER INFORMATION: Synthetic construct

<400> SEQUENCE: 8

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Ser Gly Asp Pro Pro Pro Ser
        35

<210> SEQ ID NO 9
<211> LENGTH: 39
<212> TYPE: PRT
```

<213> ORGANISM: Artificial
<220> FEATURE:
<223> OTHER INFORMATION: synthetic construct

<400> SEQUENCE: 9

His Val Glu Gly Thr Phe Thr Ser Asp Val Ser Ser Tyr Leu Glu Glu
1               5                   10                  15
Gln Ala Ala Lys Glu Phe Ile Ala Trp Leu Val Lys Gly Arg Pro Ser
            20                  25                  30
Ser Gly Asp Pro Pro Pro Ser
        35

<210> SEQ ID NO 10
<211> LENGTH: 39
<212> TYPE: PRT
<213> ORGANISM: Artificial
<220> FEATURE:
<223> OTHER INFORMATION: synthetic construct

<400> SEQUENCE: 10

His Val Glu Gly Thr Phe Thr Ser Asp Val Ser Ser Tyr Leu Glu Glu
1               5                   10                  15
Gln Ala Ala Lys Glu Phe Ile Ala Trp Leu Ile Lys Gly Gly Pro Ser
            20                  25                  30
Ser Gly Asp Pro Pro Pro Ser
        35

<210> SEQ ID NO 11
<211> LENGTH: 39
<212> TYPE: PRT
<213> ORGANISM: Artificial
<220> FEATURE:
<223> OTHER INFORMATION: synthetic construct

<400> SEQUENCE: 11

His Val Glu Gly Thr Phe Thr Ser Asp Val Ser Ser Tyr Leu Glu Glu
1               5                   10                  15
Gln Ala Ala Lys Glu Phe Ile Ala Trp Leu Val Lys Gly Arg Pro Ser
            20                  25                  30
Ser Gly Ala Pro Pro Pro Ser
        35

<210> SEQ ID NO 12
<211> LENGTH: 39
<212> TYPE: PRT
<213> ORGANISM: Artificial
<220> FEATURE:
<223> OTHER INFORMATION: synthetic construct

<400> SEQUENCE: 12

His Val Glu Gly Thr Phe Thr Ser Asp Val Ser Ser Tyr Leu Glu Glu
1               5                   10                  15
Gln Ala Ala Lys Glu Phe Ile Ala Trp Leu Ile Lys Gly Gly Pro Ser
            20                  25                  30
Ser Gly Ala Pro Pro Pro Ser
        35

<210> SEQ ID NO 13
<211> LENGTH: 39
<212> TYPE: PRT
<213> ORGANISM: Artificial
<220> FEATURE:
<223> OTHER INFORMATION: synthetic construct -continued

<400> SEQUENCE: 13

His Val Glu Gly Thr Phe Thr Ser Asp Val Ser Ser Tyr Leu Glu Glu
1               5                   10                  15

Gln Ala Val Lys Glu Phe Ile Ala Trp Leu Ile Lys Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: Artificial
<220> FEATURE:
<223> OTHER INFORMATION: synthetic construct

<400> SEQUENCE: 14

His Val Glu Gly Thr Phe Thr Ser Asp Val Ser Ser Tyr Leu Glu Glu
1               5                   10                  15

Gln Ala Val Lys Glu Phe Ile Ala Trp Leu Val Lys Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial
<220> FEATURE:
<223> OTHER INFORMATION: synthetic construct

<400> SEQUENCE: 15

His Val Glu Gly Thr Phe Thr Ser Asp Val Ser Ser Tyr Leu Glu Glu
1               5                   10                  15

Gln Ala Val Lys Glu Phe Ile Ala Trp Leu Ile Lys Gly Gly Pro Ser
            20                  25                  30

Ser Gly Asp Pro Pro Pro Ser
        35

<210> SEQ ID NO 16
<211> LENGTH: 39
<212> TYPE: PRT
<213> ORGANISM: Artificial
<220> FEATURE:
<223> OTHER INFORMATION: synthetic construct

<400> SEQUENCE: 16

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Gly Ser
            20                  25                  30

Ser Gly Asp Pro Pro Pro Ser
        35

<210> SEQ ID NO 17
<211> LENGTH: 39
<212> TYPE: PRT
<213> ORGANISM: Artificial
<220> FEATURE:
<223> OTHER INFORMATION: synthetic construct

<400> SEQUENCE: 17

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Pro Gly Ser
                20                  25                  30

Ser Gly Asp Pro Pro Pro Ser
            35

<210> SEQ ID NO 18
<211> LENGTH: 39
<212> TYPE: PRT
<213> ORGANISM: Artificial
<220> FEATURE:
<223> OTHER INFORMATION: synthetic construct

<400> SEQUENCE: 18

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Ser Pro
                20                  25                  30

Ser Gly Asp Pro Pro Pro Ser
            35

<210> SEQ ID NO 19
<211> LENGTH: 38
<212> TYPE: PRT
<213> ORGANISM: Artificial
<220> FEATURE:
<223> OTHER INFORMATION: synthetic construct

<400> SEQUENCE: 19

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
                20                  25                  30

Ser Gly Asp Pro Pro Ser
            35

<210> SEQ ID NO 20
<211> LENGTH: 39
<212> TYPE: PRT
<213> ORGANISM: Artificial
<220> FEATURE:
<223> OTHER INFORMATION: synthetic construct

<400> SEQUENCE: 20

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
                20                  25                  30

Ser Gly Asp Pro Pro Pro Ser
            35

<210> SEQ ID NO 21
<211> LENGTH: 39
<212> TYPE: PRT
<213> ORGANISM: Artificial
<220> FEATURE:
<223> OTHER INFORMATION: synthetic construct

<400> SEQUENCE: 21

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Asp Ala Pro Pro Ser
            35

<210> SEQ ID NO 22
<211> LENGTH: 39
<212> TYPE: PRT
<213> ORGANISM: Artificial
<220> FEATURE:
<223> OTHER INFORMATION: synthetic construct

<400> SEQUENCE: 22

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Asp Pro Ala Pro Ser
            35

<210> SEQ ID NO 23
<211> LENGTH: 39
<212> TYPE: PRT
<213> ORGANISM: Artificial
<220> FEATURE:
<223> OTHER INFORMATION: synthetic construct

<400> SEQUENCE: 23

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Asp Pro Pro Ala Ser
            35

<210> SEQ ID NO 24
<211> LENGTH: 39
<212> TYPE: PRT
<213> ORGANISM: Artificial
<220> FEATURE:
<223> OTHER INFORMATION: synthetic construct

<400> SEQUENCE: 24

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Asp Ala Ala Ala Ser
            35

<210> SEQ ID NO 25
<211> LENGTH: 39
<212> TYPE: PRT
<213> ORGANISM: Artificial
<220> FEATURE:
<223> OTHER INFORMATION: synthetic construct

<400> SEQUENCE: 25

His Val Glu Gly Thr Phe Thr Ser Asp Trp Ser Ser Tyr Leu Glu Gly
1               5                   10                  15

Gln Ala Ala Lys Glu Phe Ile Ala Trp Leu Ile Lys Gly Gly Pro Ser
            20                  25                  30

```
Ser Gly Ala Pro Pro Ser
        35

<210> SEQ ID NO 26
<211> LENGTH: 39
<212> TYPE: PRT
<213> ORGANISM: Artificial
<220> FEATURE:
<223> OTHER INFORMATION: synthetic construct

<400> SEQUENCE: 26

His Val Glu Gly Thr Phe Thr Ser Asp Trp Ser Ser Tyr Leu Glu Gly
1               5                   10                  15

Gln Ala Ala Lys Glu Phe Ile Ala Trp Leu Ile Lys Gly Gly Pro Ser
            20                  25                  30

Ser Gly Ala Pro Pro His
        35

<210> SEQ ID NO 27
<211> LENGTH: 39
<212> TYPE: PRT
<213> ORGANISM: Artificial
<220> FEATURE:
<223> OTHER INFORMATION: synthetic construct

<400> SEQUENCE: 27

His Val Glu Gly Thr Phe Thr Ser Asp Val Ser Ser Tyr Leu Glu Gly
1               5                   10                  15

Gln Ala Ala Lys Glu Phe Ile Ala Trp Leu Ile Lys Gly Gly Pro Ser
            20                  25                  30

Ser Gly Ala Pro Pro Ser
        35

<210> SEQ ID NO 28
<211> LENGTH: 39
<212> TYPE: PRT
<213> ORGANISM: Artificial
<220> FEATURE:
<223> OTHER INFORMATION: synthetic construct

<400> SEQUENCE: 28

His Val Glu Gly Thr Phe Thr Ser Asp Val Ser Ser Tyr Leu Glu Gly
1               5                   10                  15

Gln Ala Ala Lys Glu Phe Ile Ala Trp Leu Ile Lys Gly Gly Pro Ser
            20                  25                  30

Ser Gly Asp Pro Pro Ser
        35

<210> SEQ ID NO 29
<211> LENGTH: 40
<212> TYPE: PRT
<213> ORGANISM: Artificial
<220> FEATURE:
<223> OTHER INFORMATION: synthetic construct

<400> SEQUENCE: 29

His Val Glu Gly Thr Phe Thr Ser Asp Trp Ser Ser Tyr Leu Glu Gly
1               5                   10                  15

Gln Ala Ala Lys Glu Phe Ile Ala Trp Leu Ile Lys Gly Gly Pro Ser
            20                  25                  30

Ser Gly Ala Pro Pro Ser His
        35                  40
```

```
<210> SEQ ID NO 30
<211> LENGTH: 40
<212> TYPE: PRT
<213> ORGANISM: Artificial
<220> FEATURE:
<223> OTHER INFORMATION: synthetic construct

<400> SEQUENCE: 30

His Val Glu Gly Thr Phe Thr Ser Asp Trp Ser Ser Tyr Leu Glu Gly
1               5                   10                  15

Gln Ala Ala Lys Glu Phe Ile Ala Trp Leu Ile Lys Gly Gly Pro His
            20                  25                  30

Ser Ser Gly Ala Pro Pro Pro Ser
        35                  40

<210> SEQ ID NO 31
<211> LENGTH: 39
<212> TYPE: PRT
<213> ORGANISM: Artificial
<220> FEATURE:
<223> OTHER INFORMATION: synthetic construct

<400> SEQUENCE: 31

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Ser
            20                  25                  30

Ser Gly Ala Pro Pro Pro Ser
        35

<210> SEQ ID NO 32
<211> LENGTH: 39
<212> TYPE: PRT
<213> ORGANISM: Artificial
<220> FEATURE:
<223> OTHER INFORMATION: synthetic construct

<400> SEQUENCE: 32

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Pro Ser
            20                  25                  30

Ser Gly Ala Pro Pro Pro Ser
        35

<210> SEQ ID NO 33
<211> LENGTH: 39
<212> TYPE: PRT
<213> ORGANISM: Artificial
<220> FEATURE:
<223> OTHER INFORMATION: synthetic construct

<400> SEQUENCE: 33

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

Ser Gly Ala Pro Pro Pro Ser
        35

<210> SEQ ID NO 34
<211> LENGTH: 39
```

```
<212> TYPE: PRT
<213> ORGANISM: Artificial
<220> FEATURE:
<223> OTHER INFORMATION: synthetic construct

<400> SEQUENCE: 34

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Ser Gly Ala Pro Pro Pro Ser
        35

<210> SEQ ID NO 35
<211> LENGTH: 39
<212> TYPE: PRT
<213> ORGANISM: Artificial
<220> FEATURE:
<223> OTHER INFORMATION: synthetic construct

<400> SEQUENCE: 35

His Val Glu Gly Thr Phe Thr Ser Asp Val Ser Ser Tyr Leu Glu Glu
1               5                   10                  15

Gln Ala Val Lys Glu Phe Ile Ala Trp Leu Ile Lys Gly Arg Gly Ser
            20                  25                  30

Ser Gly Ala Pro Pro Pro Ser
        35

<210> SEQ ID NO 36
<211> LENGTH: 39
<212> TYPE: PRT
<213> ORGANISM: Artificial
<220> FEATURE:
<223> OTHER INFORMATION: synthetic construct

<400> SEQUENCE: 36

His Val Glu Gly Thr Phe Thr Ser Asp Trp Ser Ser Tyr Leu Glu Glu
1               5                   10                  15

Gln Ala Ala Lys Glu Phe Ile Ala Trp Leu Ile Lys Gly Arg Gly Ser
            20                  25                  30

Ser Gly Ala Pro Pro Pro Ser
        35

<210> SEQ ID NO 37
<211> LENGTH: 40
<212> TYPE: PRT
<213> ORGANISM: Artificial
<220> FEATURE:
<223> OTHER INFORMATION: synthetic construct

<400> SEQUENCE: 37

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Arg Gly His
            20                  25                  30

Ser Ser Gly Ala Pro Pro Pro Ser
        35                  40

<210> SEQ ID NO 38
<211> LENGTH: 40
<212> TYPE: PRT
<213> ORGANISM: Artificial
<220> FEATURE:
```

<223> OTHER INFORMATION: synthetic construct

<400> SEQUENCE: 38

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly His
            20                  25                  30

Ser Ser Gly Ala Pro Pro Pro Ser
        35                  40

<210> SEQ ID NO 39
<211> LENGTH: 41
<212> TYPE: PRT
<213> ORGANISM: Artificial
<220> FEATURE:
<223> OTHER INFORMATION: synthetic construct

<400> SEQUENCE: 39

His Val Glu Gly Thr Phe Thr Ser Asp Trp Ser Ser Tyr Leu Glu Glu
1               5                   10                  15

Gln Ala Ala Lys Glu Phe Ile Ala Trp Leu Ile Lys Gly Gly Pro His
            20                  25                  30

Ser Ser Gly Ala Pro Pro Pro Ser His
        35                  40

<210> SEQ ID NO 40
<211> LENGTH: 40
<212> TYPE: PRT
<213> ORGANISM: Artificial
<220> FEATURE:
<223> OTHER INFORMATION: synthetic construct

<400> SEQUENCE: 40

His Val Glu Gly Thr Phe Thr Ser Asp Trp Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Ala Pro Pro Pro Ser His
        35                  40

<210> SEQ ID NO 41
<211> LENGTH: 40
<212> TYPE: PRT
<213> ORGANISM: Artificial
<220> FEATURE:
<223> OTHER INFORMATION: synthetic construct

<400> SEQUENCE: 41

His Val Glu Gly Thr Phe Thr Ser Asp Val Ser Trp Tyr Leu Glu Gly
1               5                   10                  15

Gln Ala Val Lys Glu Phe Ile Ala Trp Leu Ile Lys Gly Gly Pro His
            20                  25                  30

Ser Ser Gly Ala Pro Pro Pro Ser
        35                  40

<210> SEQ ID NO 42
<211> LENGTH: 39
<212> TYPE: PRT
<213> ORGANISM: Artificial
<220> FEATURE:
<223> OTHER INFORMATION: synthetic construct

<400> SEQUENCE: 42

His Val Glu Gly Thr Phe Thr Ser Asp Val Ser Ser Tyr Leu Glu Glu
1               5                   10                  15

Gln Ala Val Lys Glu Phe Ile Ala Trp Leu Ile Lys Gly Gly Pro Ser
            20                  25                  30

Ser Gly Ala Pro Pro Ser
            35

<210> SEQ ID NO 43
<211> LENGTH: 40
<212> TYPE: PRT
<213> ORGANISM: Artificial
<220> FEATURE:
<223> OTHER INFORMATION: synthetic construct

<400> SEQUENCE: 43

His Val Glu Gly Thr Phe Thr Ser Asp Val Ser Ser Tyr Leu Glu Glu
1               5                   10                  15

Gln Ala Val Lys Glu Phe Ile Ala Trp Leu Ile Lys Gly Gly Pro Ser
            20                  25                  30

Ser Gly Ala Pro Pro Ser His
            35              40

<210> SEQ ID NO 44
<211> LENGTH: 39
<212> TYPE: PRT
<213> ORGANISM: Artificial
<220> FEATURE:
<223> OTHER INFORMATION: synthetic construct

<400> SEQUENCE: 44

His Val Glu Gly Thr Phe Thr Ser Asp Trp Ser Ser Tyr Leu Glu Glu
1               5                   10                  15

Gln Ala Val Lys Glu Phe Ile Ala Trp Leu Ile Lys Gly Gly Pro Ser
            20                  25                  30

Ser Gly Ala Pro Pro Ser
            35

<210> SEQ ID NO 45
<211> LENGTH: 40
<212> TYPE: PRT
<213> ORGANISM: Artificial
<220> FEATURE:
<223> OTHER INFORMATION: synthetic construct

<400> SEQUENCE: 45

His Val Glu Gly Thr Phe Thr Ser Asp Trp Ser Ser Tyr Leu Glu Glu
1               5                   10                  15

Gln Ala Val Lys Glu Phe Ile Ala Trp Leu Ile Lys Gly Gly Pro Ser
            20                  25                  30

Ser Gly Ala Pro Pro Ser His
            35              40

<210> SEQ ID NO 46
<211> LENGTH: 40
<212> TYPE: PRT
<213> ORGANISM: Artificial
<220> FEATURE:
<223> OTHER INFORMATION: synthetic construct

<400> SEQUENCE: 46

His Val Glu Gly Thr Phe Thr Ser Asp Trp Ser Ser Tyr Leu Glu Glu
1               5                   10                  15

```
Gln Ala Val Lys Glu Phe Ile Ala Trp Leu Ile Lys Gly Gly Pro His
            20                  25                  30

Ser Ser Gly Ala Pro Pro Ser
        35                  40
```

<210> SEQ ID NO 47
<211> LENGTH: 40
<212> TYPE: PRT
<213> ORGANISM: Artificial
<220> FEATURE:
<223> OTHER INFORMATION: synthetic construct

<400> SEQUENCE: 47

```
His Val Glu Gly Thr Phe Thr Ser Asp Trp Ser Lys Tyr Leu Glu Glu
1               5                   10                  15

Gln Ala Val Lys Glu Phe Ile Ala Trp Leu Ile Lys Gly Gly Pro Ser
            20                  25                  30

Ser Gly Ala Pro Pro Ser His
        35                  40
```

<210> SEQ ID NO 48
<211> LENGTH: 40
<212> TYPE: PRT
<213> ORGANISM: Artificial
<220> FEATURE:
<223> OTHER INFORMATION: synthetic construct

<400> SEQUENCE: 48

```
His Val Glu Gly Thr Phe Thr Ser Asp Val Ser Ser Tyr Leu Glu Glu
1               5                   10                  15

Gln Ala Val Lys Glu Phe Ile Ala Trp Leu Ile Lys Gly Gly Pro Ser
            20                  25                  30

Ser Gly Ala Pro Pro Arg Gly
        35                  40
```

<210> SEQ ID NO 49
<211> LENGTH: 40
<212> TYPE: PRT
<213> ORGANISM: Artificial
<220> FEATURE:
<223> OTHER INFORMATION: synthetic construct

<400> SEQUENCE: 49

```
His Val Glu Gly Thr Phe Thr Ser Asp Val Ser Ser Tyr Leu Glu Glu
1               5                   10                  15

Gln Ala Val Lys Glu Phe Ile Ala Trp Leu Ile Lys Gly Gly Pro Ser
            20                  25                  30

Ser Gly Ala Pro Pro Arg Gly
        35                  40
```

<210> SEQ ID NO 50
<211> LENGTH: 39
<212> TYPE: PRT
<213> ORGANISM: Artificial
<220> FEATURE:
<223> OTHER INFORMATION: synthetic construct

<400> SEQUENCE: 50

```
His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30
```

Ser Gly Ala Pro Pro Ser
        35

<210> SEQ ID NO 51
<211> LENGTH: 39
<212> TYPE: PRT
<213> ORGANISM: Artificial
<220> FEATURE:
<223> OTHER INFORMATION: synthetic construct

<400> SEQUENCE: 51

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Asp Gly Gly Pro Ser
            20                  25                  30

Ser Gly Arg Pro Pro Pro Ser
        35

<210> SEQ ID NO 52
<211> LENGTH: 39
<212> TYPE: PRT
<213> ORGANISM: Artificial
<220> FEATURE:
<223> OTHER INFORMATION: synthetic construct

<400> SEQUENCE: 52

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Asp Gly Gly Pro Ser
            20                  25                  30

Ser Gly Arg Pro Pro Ser
        35

<210> SEQ ID NO 53
<211> LENGTH: 39
<212> TYPE: PRT
<213> ORGANISM: Artificial
<220> FEATURE:
<223> OTHER INFORMATION: synthetic construct

<400> SEQUENCE: 53

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Asp Gly Gly Pro Ser
            20                  25                  30

Ser Gly Lys Pro Pro Pro Ser
        35

<210> SEQ ID NO 54
<211> LENGTH: 36
<212> TYPE: PRT
<213> ORGANISM: Artificial
<220> FEATURE:
<223> OTHER INFORMATION: synthetic construct

<400> SEQUENCE: 54

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Asp Gly Gly Pro Ser
            20                  25                  30

Ser Gly Arg Gly
        35

<210> SEQ ID NO 55
<211> LENGTH: 39
<212> TYPE: PRT
<213> ORGANISM: Artificial
<220> FEATURE:
<223> OTHER INFORMATION: synthetic construct

<400> SEQUENCE: 55

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Ala Pro Pro Pro Ser
        35

<210> SEQ ID NO 56
<211> LENGTH: 39
<212> TYPE: PRT
<213> ORGANISM: Artificial
<220> FEATURE:
<223> OTHER INFORMATION: synthetic construct

<400> SEQUENCE: 56

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

Trp Gly Ala Pro Pro Pro Ser
        35

<210> SEQ ID NO 57
<211> LENGTH: 41
<212> TYPE: PRT
<213> ORGANISM: Artificial
<220> FEATURE:
<223> OTHER INFORMATION: synthetic construct

<400> SEQUENCE: 57

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Ala Pro Pro Pro Gly Pro Ser
        35                  40

<210> SEQ ID NO 58
<211> LENGTH: 44
<212> TYPE: PRT
<213> ORGANISM: Artificial
<220> FEATURE:
<223> OTHER INFORMATION: synthetic construct

<400> SEQUENCE: 58

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Ala Pro Pro Pro Gly Pro Ser Gly Pro Ser
        35                  40

<210> SEQ ID NO 59

```
<211> LENGTH: 31
<212> TYPE: PRT
<213> ORGANISM: Artificial
<220> FEATURE:
<223> OTHER INFORMATION: synthetic construct

<400> SEQUENCE: 59

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 60
<211> LENGTH: 44
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (32)..(32)
<223> OTHER INFORMATION: Xaa is Ser, Pro, or His
<220> FEATURE:
<221> NAME/KEY: MISC_FEATURE
<222> LOCATION: (33)..(33)
<223> OTHER INFORMATION: Xaa is Ser, Arg, Thr, Trp, or Lys
<220> FEATURE:
<221> NAME/KEY: MISC_FEATURE
<222> LOCATION: (34)..(34)
<223> OTHER INFORMATION: Xaa is Ser or Gly
<220> FEATURE:
<221> NAME/KEY: MISC_FEATURE
<222> LOCATION: (35)..(35)
<223> OTHER INFORMATION: Xaa is Ala, Asp, Arg, Glu, Lys, Gly or a
      Modified Residue
<220> FEATURE:
<221> NAME/KEY: MOD_RES
<222> LOCATION: (35)..(35)
<223> OTHER INFORMATION: AMIDATION
<220> FEATURE:
<221> NAME/KEY: MISC_FEATURE
<222> LOCATION: (36)..(36)
<223> OTHER INFORMATION: Xaa is Pro, Ala, Absent or a Modified Residue
<220> FEATURE:
<221> NAME/KEY: MOD_RES
<222> LOCATION: (36)..(36)
<223> OTHER INFORMATION: AMIDATION
<220> FEATURE:
<221> NAME/KEY: MISC_FEATURE
<222> LOCATION: (37)..(37)
<223> OTHER INFORMATION: Xaa is Pro, Ala, Absent or a Modified Residue
<220> FEATURE:
<221> NAME/KEY: MOD_RES
<222> LOCATION: (37)..(37)
<223> OTHER INFORMATION: AMIDATION
<220> FEATURE:
<221> NAME/KEY: MISC_FEATURE
<222> LOCATION: (38)..(38)
<223> OTHER INFORMATION: Xaa is Pro, Ala, Arg, Lys, His, Absent or a
      Modified Residue
<220> FEATURE:
<221> NAME/KEY: MOD_RES
<222> LOCATION: (38)..(38)
<223> OTHER INFORMATION: AMIDATION
<220> FEATURE:
<221> NAME/KEY: MISC_FEATURE
<222> LOCATION: (39)..(39)
<223> OTHER INFORMATION: Xaa is Ser, His, Pro, Lys, Arg, Gly, Absent or
      a Modified Residue
<220> FEATURE:
<221> NAME/KEY: MOD_RES
<222> LOCATION: (39)..(39)
<223> OTHER INFORMATION: AMIDATION
<220> FEATURE:
<221> NAME/KEY: MISC_FEATURE
<222> LOCATION: (40)..(40)
```

```
<223> OTHER INFORMATION: Xaa is His, Ser, Arg, Lys, Pro, Gly, Absent or
      a Modified Residue
<220> FEATURE:
<221> NAME/KEY: MOD_RES
<222> LOCATION: (40)..(40)
<223> OTHER INFORMATION: AMIDATION
<220> FEATURE:
<221> NAME/KEY: MISC_FEATURE
<222> LOCATION: (41)..(41)
<223> OTHER INFORMATION: Xaa is His, Ser, Arg, Lys, Absent or a
      Modified Residue
<220> FEATURE:
<221> NAME/KEY: MOD_RES
<222> LOCATION: (41)..(41)
<223> OTHER INFORMATION: AMIDATION
<220> FEATURE:
<221> NAME/KEY: MISC_FEATURE
<222> LOCATION: (42)..(42)
<223> OTHER INFORMATION: Xaa is Gly, His, Absent or a Modified Residue
<220> FEATURE:
<221> NAME/KEY: MOD_RES
<222> LOCATION: (42)..(42)
<223> OTHER INFORMATION: AMIDATION
<220> FEATURE:
<221> NAME/KEY: MISC_FEATURE
<222> LOCATION: (43)..(43)
<223> OTHER INFORMATION: Xaa is Pro, His, Absent or a Modified Residue
<220> FEATURE:
<221> NAME/KEY: MOD_RES
<222> LOCATION: (43)..(43)
<223> OTHER INFORMATION: AMIDATION
<220> FEATURE:
<221> NAME/KEY: MISC_FEATURE
<222> LOCATION: (44)..(44)
<223> OTHER INFORMATION: Xaa is Ser, His, Absent or a Modified Residue
<220> FEATURE:
<221> NAME/KEY: MOD_RES
<222> LOCATION: (44)..(44)
<223> OTHER INFORMATION: AMIDATION

<400> SEQUENCE: 60

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Pro Xaa
            20                  25                  30

Xaa Xaa Xaa Xaa Xaa Xaa Xaa Xaa Xaa Xaa Xaa Xaa
        35                  40

<210> SEQ ID NO 61
<211> LENGTH: 41
<212> TYPE: PRT
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
```

-continued

```
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(41)
<223> OTHER INFORMATION: Xaa can be any naturally occurring amino acid

<400> SEQUENCE: 61

Xaa Xaa Glu Gly Thr Xaa Thr Ser Asp Xaa Ser Xaa Xaa Xaa Glu Xaa
 1               5                  10                  15

Gln Ala Xaa Lys Xaa Phe Ile Xaa Trp Leu Xaa Xaa Gly Xaa Xaa Xaa
            20                  25                  30

Xaa Xaa Xaa Xaa Xaa Xaa Xaa Xaa Xaa
        35                  40
```

EXTENDED GLUCAGON-LIKE PEPTIDE-1 ANALOGS

This is the national phase application, under 35 USC 371, for PCT/US03/00001 filed Jan. 3, 2003, which claims the priority of U.S. provisional application No. 60/346,474 filed Jan. 8, 2002 and U.S. provisional application No. 60/405,097, filed Aug. 21, 2002.

A large body of pre-clinical and clinical research data suggests that glucagon-like peptide-1 (GLP-1) shows great promise as a treatment for non-insulin dependent diabetes mellitus (NIDDM) especially when oral agents begin to fail. GLP-1 induces numerous biological effects such as stimulating insulin secretion, inhibiting glucagon secretion, inhibiting gastric emptying, enhancing glucose utilization, and inducing weight loss. Further, pre-clinical studies suggest that GLP-1 may also act to prevent the pancreatic β cell deterioration that occurs as the disease progresses. Perhaps the most salient characteristic of GLP-1 is its ability to stimulate insulin secretion without the associated risk of hypoglycemia that is seen when using insulin therapy or some types of oral therapies that act by increasing insulin expression. As NIDDM progresses, it becomes extremely important to achieve near normal glycemic control and thereby minimize the complications associated with prolonged hyperglycemia. GLP-1 would appear to be the drug of choice. However, the usefulness of therapy involving GLP-1 peptides has been limited by the fact that GLP-1(1-37) is poorly active, and the two naturally occurring truncated peptides, GLP-1(7-37)OH and GLP-1(7-36)NH$_2$, are rapidly cleared in vivo and have extremely short in vivo half-lives.

Further, GLP-1 peptides currently in development cannot be given orally and, like insulin, must be injected. Thus, despite the clear medical advantages associated with therapy involving GLP-1, the short half-life which results in a drug that must be injected one or more times a day has impeded commercial development efforts.

It is known that endogenously produced dipeptidyl-peptidase IV (DPP-IV) inactivates circulating GLP-1 peptides by removing the N-terminal histidine and alanine residues and is a major reason for the short in vivo half-life. Thus, recent efforts have focused on the development of GLP-1 peptides that are resistant to DPP-IV degradation. Some of these resistant peptides have modifications at the N-terminus (See U.S. Pat. No. 5,705,483), and some are derivatized GLP-1 peptides wherein large acyl groups that prevent DPP-IV from accessing the N-terminus of the peptide are attached to various amino acids (See WO 98/08871).

The present invention, however, provides a different approach to the development of biologically active GLP-1 peptides that persist in the serum for extended periods. The GLP-1 peptides of the present invention are analogs of GLP-1(7-37) wherein various amino acids are added to the C-terminus of the analog. These extended GLP-1 peptides not only have serum half-lives that are much longer than the native molecules but are particularly suited for oral and pulmonary administration due to their resistance to various proteolytic enzymes found in the stomach, intestine, and lungs. Further, many of these extended GLP-1 peptides are more potent than the native molecules. This increased potency coupled with resistance to various proteases facilitates the use of delivery technology associated with limited bioavailability. Thus, the present invention makes possible non-injectable therapy which involves delivering cost-effective amounts of biologically active GLP-1 peptides such that therapeutic serum levels are achieved.

It has now been found that a number of GLP-1 peptides with modifications at various positions coupled with an extended C-terminus show increased stability compared to some DPP-IV resistant GLP-1 molecules such as Val[8]-GLP-1(7-37)OH. Many of these extended GLP-1 peptides are more potent as well.

One embodiment of the present invention is a GLP-1 peptide comprising the amino acid sequence of formula 1 (SEQ ID NO:1)

(SEQ ID NO: 1)
Xaa$_7$-Xaa$_8$-Glu-Gly-Thr-Xaa$_{12}$-Thr-Ser-Asp-Xaa$_{16}$-Ser-

Xaa$_{18}$-Xaa$_{19}$-Xaa$_{20}$-Glu-Xaa$_{22}$-Gln-Ala-Xaa$_{25}$-Lys-

Xaa$_{27}$-Phe-Ile-Xaa$_{30}$-Trp-Leu-Xaa$_{33}$-Xaa$_{34}$-Gly-Xaa$_{36}$-

Xaa$_{37}$-Xaa$_{38}$-Xaa$_{39}$-Xaa$_{40}$-Xaa$_{41}$-Xaa$_{42}$-Xaa$_{43}$-Xaa$_{44}$-

Xaa$_{45}$-Xaa$_{46}$-Xaa$_{47}$-Xaa$_{48}$-Xaa$_{49}$-Xaa$_{50}$

Formula 1 wherein:
Xaa$_7$ is: L-histidine, D-histidine, desamino-histidine, 2-amino-histidine, β-hydroxy-histidine, homohistidine, α-fluoromethyl-histidine, or α-methyl-histidine;
Xaa$_8$ is: Ala, Gly, Val, Leu, Ile, Ser, or Thr;
Xaa$_{12}$ is: Phe, Trp, or Tyr;
Xaa$_{16}$ is: Val, Trp, Ile, Leu, Phe, or Tyr;
Xaa$_{18}$ is: Ser, Trp, Tyr, Phe, Lys, Ile, Leu, Val;
Xaa$_{19}$ is: Tyr, Trp, or Phe;
Xaa$_{20}$ is: Leu, Phe, Tyr, or Trp;
Xaa$_{22}$ is: Gly, Glu, Asp, or Lys;
Xaa$_{25}$ is: Ala, Val, Ile, or Leu;
Xaa$_{27}$ is: Glu, Ile, or Ala;
Xaa$_{30}$ is: Ala or Glu;
Xaa$_{33}$ is: Val or Ile;
Xaa$_{34}$ is: Lys, Asp, Arg, or Glu;
Xaa$_{36}$ is: Gly, Pro, or Arg;
Xaa$_{37}$ is: Gly, Pro, or Ser;
Xaa$_{38}$ is: Ser, Pro, or His;
Xaa$_{39}$ is: Ser, Arg, Thr, Trp, or Lys;
Xaa$_{40}$ is: Ser or Gly;
Xaa$_{41}$ is: Ala, Asp, Arg, Glu, Lys, or Gly;
Xaa$_{42}$ is: Pro, Ala, NH$_2$, or is absent;
Xaa$_{43}$ is: Pro, Ala, NH$_2$, or is absent;
Xaa$_{44}$ is: Pro, Ala, Arg, Lys, His, NH$_2$, or is absent;
Xaa$_{45}$ is: Ser, His, Pro, Lys, Arg, Gly, NH$_2$ or is absent;
Xaa$_{46}$ is: His, Ser, Arg, Lys, Pro, Gly, NH$_2$ or is absent; and
Xaa$_{47}$ is: His, Ser, Arg, Lys, NH$_2$ or is absent;
Xaa$_{48}$ is: Gly, His, NH$_2$ or is absent;
Xaa$_{49}$ is: Pro, His, NH$_2$ or is absent; and
Xaa$_{50}$ is: Ser, His, Ser-NH$_2$, His-NH$_2$ or is absent;

provided that if Xaa$_{42}$, Xaa$_{43}$, Xaa$_{44}$, Xaa$_{45}$, Xaa$_{46}$, Xaa$_{47}$, Xaa$_{48}$, or Xaa$_{49}$ is absent each amino acid downstream is absent and further provided that the if Xaa$_{36}$ is Arg and Xaa$_{37}$ is Gly or Ser, the GLP-1 peptide does not have the following C-terminal amino acid extension beginning at Xaa$_{38}$: Ser-Ser-Gly-Ala-Pro-Pro-Pro-Ser-NH$_2$.

Another embodiment of the present invention is a GLP-1 peptide comprising the amino acid sequence of formula 2 (SEQ ID NO:2)

(SEQ ID NO: 2)
Xaa$_7$-Xaa$_8$-Glu-Gly-Thr-Xaa$_{12}$-Thr-Ser-Asp-Xaa$_{16}$-Ser-

Xaa$_{18}$-Xaa$_{19}$-Xaa$_{20}$-Glu-Xaa$_{22}$-Gln-Ala-Xaa$_{25}$-Lys-

Xaa$_{27}$-Phe-Ile-Xaa$_{30}$-Trp-Leu-Xaa$_{33}$-Xaa$_{34}$-Gly-Xaa$_{36}$-

-continued

Xaa$_{37}$-Xaa$_{38}$-Xaa$_{39}$-Xaa$_{40}$-Xaa$_{41}$-Xaa$_{42}$-Xaa$_{43}$-Xaa$_{44}$-

Xaa$_{45}$-Xaa$_{46}$-Xaa$_{47}$

Formula 2 wherein:

Xaa$_7$ is: L-histidine, D-histidine, desamino-histidine, 2-amino-histidine, β-hydroxy-histidine, homohistidine, α-fluoromethyl-histidine, or α-methyl-histidine;
Xaa$_8$ is: Ala, Gly, Val, Leu, Ile, Ser, or Thr;
Xaa$_{12}$ is: Phe, Trp, or Tyr;
Xaa$_{16}$ is: Val, Trp, Ile, Leu, Phe, or Tyr;
Xaa$_{18}$ is: Ser, Trp, Tyr, Phe, Lys, Ile, Leu, or Val;
Xaa$_{19}$ is: Tyr, Trp, or Phe;
Xaa$_{20}$ is: Leu, Phe, Tyr, or Trp;
Xaa$_{22}$ is: Gly, Glu, Asp, or Lys;
Xaa$_{25}$ is: Ala, Val, Ile, or Leu;
Xaa$_{27}$ is: Glu, Ile, or Ala;
Xaa$_{30}$ is: Ala or Glu
Xaa$_{33}$ is: Val or Ile;
Xaa$_{34}$ is: Lys, Asp, Arg, or Glu;
Xaa$_{36}$ is: Gly, Pro, or Arg;
Xaa$_{37}$ is: Gly, Pro, or Ser;
Xaa$_{38}$ is: Ser, Pro, or His;
Xaa$_{39}$ is: Ser, Arg, Thr, Trp, or Lys;
Xaa$_{40}$ is: Ser or Gly;
Xaa$_{41}$ is: Ala, Asp, Arg, Glu, Lys, or Gly;
Xaa$_{42}$ is: Pro, Ala, NH$_2$, or is absent;
Xaa$_{43}$ is: Pro, Ala, NH$_2$, or is absent;
Xaa$_{44}$ is: Pro, Ala, Arg, Lys, His, NH$_2$, or is absent;
Xaa$_{45}$ is: Ser, His, Pro, Lys, Arg, NH$_2$ or is absent;
Xaa$_{46}$ is: His, Ser, Arg, Lys, NH$_2$ or is absent; and
Xaa$_{47}$ is: His, Ser, Arg, Lys, NH$_2$ or is absent;

provided that if Xaa$_{42}$, Xaa$_{43}$, Xaa$_{44}$, Xaa$_{45}$, Xaa$_{46}$, or Xaa$_{47}$ is absent each amino acid downstream is absent and further provided that if Xaa$_{36}$ is Arg and Xaa$_{37}$ is Gly or Ser, the GLP-1 peptide does not have the following C-terminal amino acid extension beginning at Xaa$_{38}$: Ser-Ser-Gly-Ala-Pro-Pro-Pro-Ser-NH$_2$.

Another embodiment of the present invention is an extended GLP-1 peptide comprising the amino acid sequence of formula 3 (SEQ ID NO:3)

(SEQ ID NO: 3)
Xaa$_7$-Xaa$_8$-Glu-Gly-Thr-Phe-Thr-Ser-Asp-Xaa$_{16}$-Ser-

Ser-Tyr-Lys-Glu-Xaa$_{22}$-Gln-Ala-Xaa$_{25}$-Lys-Glu-Phe-

Ile-Ala-Trp-Leu-Xaa$_{33}$-Xaa$_{34}$-Gly-Xaa$_{36}$-Xaa$_{37}$-Xaa$_{38}$-

Xaa$_{39}$-Xaa$_{40}$-Xaa$_{41}$-Xaa$_{42}$-Xaa$_{43}$-Xaa$_{44}$-Xaa$_{45}$-Xaa$_{46}$-

Xaa$_{47}$

Formula 3 wherein:

Xaa$_7$ is: L-histidine, D-histidine, desamino-histidine, 2-amino-histidine, β-hydroxy-histidine, homohistidine, α-fluoromethyl-histidine, or α-methyl-histidine;
Xaa$_8$ is: Gly, Val, Leu, Ile, Ser, or Thr;
Xaa$_{16}$ is: Val, Trp, Ile, Leu, Phe, or Tyr;
Xaa$_{22}$ is: Gly, Glu, Asp, or Lys;
Xaa$_{25}$ is: Ala, Val, Ile, or Leu;
Xaa$_{33}$ is: Val or Ile;
Xaa$_{34}$ is: Lys, Asp, Arg, or Glu;
Xaa$_{36}$ is: Gly, Pro, or Arg;
Xaa$_{37}$ is: Gly, Pro, or Ser;
Xaa$_{38}$ is: Ser, Pro, or His;
Xaa$_{39}$ is: Ser, Arg, Thr, Trp, or Lys;
Xaa$_{40}$ is: Ser or Gly;
Xaa$_{41}$ is: Ala, Asp, Arg, Glu, Lys, or Gly;
Xaa$_{42}$ is: Pro or Ala;
Xaa$_{43}$ is: Pro or Ala;
Xaa$_{44}$ is: Pro, Ala, Arg, Lys, His, NH$_2$, or is absent;
Xaa$_{45}$ is: Ser, His, Pro, Lys, Arg, NH$_2$ or is absent;
Xaa$_{46}$ is: His, Ser, Arg, Lys, NH$_2$ or is absent; and
Xaa$_{47}$ is: His, Ser, Arg, Lys, NH$_2$ or is absent;

provided that if Xaa$_{44}$, Xaa$_{45}$, Xaa$_{46}$, or Xaa$_{47}$ is absent each amino acid downstream is absent and further provided that if Xaa$_{36}$ is Arg and Xaa$_{37}$ is Gly or Ser, the GLP-1 peptide does not have the following C-terminal amino acid extension beginning at Xaa$_{38}$: Ser-Ser-Gly-Ala-Pro-Pro-Pro-Ser-NH$_2$.

Another embodiment of the present invention is an extended GLP-1 peptide comprising the amino acid sequence of formula 4 (SEQ ID NO:4)

(SEQ ID NO: 4)
Xaa$_7$-Xaa$_8$-Glu-Gly-Thr-Phe-Thr-Ser-Asp-Val-Ser-Ser-

Tyr-Lys-Glu-Xaa$_{22}$-Gln-Ala-Xaa$_{25}$-Lys-Glu-Phe-Ile-

Ala-Trp-Leu-Xaa$_{33}$-Lys-Gly-Gly-Pro-Xaa$_{38}$-Xaa$_{39}$-

Xaa$_{40}$-Xaa$_{41}$-Xaa$_{42}$-Xaa$_{43}$-Xaa$_{44}$-Xaa$_{45}$-Xaa$_{46}$-Xaa$_{47}$

Formula 4 wherein:

Xaa$_7$ is: L-histidine, D-histidine, desamino-histidine, 2-amino-histidine, β-hydroxy-histidine, homohistidine, α-fluoromethyl-histidine, or α-methyl-histidine;
Xaa$_8$ is: Gly, Val, Leu, Ile, Ser, or Thr;
Xaa$_{22}$ is: Gly, Glu, Asp, or Lys;
Xaa$_{25}$ is: Ala, Val, Ile, or Leu;
Xaa$_{33}$ is: Val or Ile;
Xaa$_{38}$ is: Ser, Pro, or His;
Xaa$_{39}$ is: Ser, Arg, Thr, Trp, or Lys;
Xaa$_{40}$ is: Ser or Gly;
Xaa$_{41}$ is: Ala, Asp, Arg, Glu, Lys, or Gly;
Xaa$_{42}$ is: Pro or Ala;
Xaa$_{43}$ is: Pro or Ala;
Xaa$_{44}$ is: Pro, Ala, Arg, Lys, His, NH$_2$, or is absent;
Xaa$_{45}$ is: Ser, His, Pro, Lys, Arg, NH$_2$ or is absent;
Xaa$_{46}$ is: His, Ser, Arg, Lys, NH$_2$ or is absent; and
Xaa$_{47}$ is: His, Ser, Arg, Lys, His-NH$_2$, Ser-NH$_2$, Arg-NH$_2$, His-NH$_2$, NH$_2$, or is absent;

provided that if Xaa$_{44}$, Xaa$_{45}$, Xaa$_{46}$, or Xaa$_{47}$ is absent each amino acid downstream is absent.

Another embodiment of the present invention is an extended GLP-1 peptide comprising an amino acid sequence of formula 5 (SEQ ID NO:60)

(SEQ ID NO: 60)
His-Ala-Glu-Gly-Thr-Phe-Thr-Ser-Asp-Val-Ser-Ser-

Tyr-Leu-Glu-Gly-Gln-Ala-Ala-Lys-Glu-Phe-Ile-Ala-

Trp-Leu-Val-Lys-Gly-Gly-Pro-Xaa$_{38}$-Xaa$_{39}$-Xaa$_{40}$-

Xaa$_{41}$-Xaa$_{42}$-Xaa$_{43}$-Xaa$_{44}$-Xaa$_{45}$-Xaa$_{46}$-Xaa$_{47}$-Xaa$_{48}$-

Xaa$_{49}$-Xaa$_{50}$

Formula 5

Wherein:

$Xaa_{38}$ is: Ser, Pro, or His;
$Xaa_{39}$ is: Ser, Arg, Thr, Trp, or Lys;
$Xaa_{40}$ is: Ser or Gly;
$Xaa_{41}$ is: Ala, Asp, Arg, Glu, Lys; or Gly;
$Xaa_{42}$ is: Pro, Ala, $NH_2$, or is absent;
$Xaa_{43}$ is: Pro, Ala, $NH_2$, or is absent;
$Xaa_{44}$ is: Pro, Ala, Arg, Lys, His, $NH_2$, or is absent;
$Xaa_{45}$ is: Ser, His, Pro, Lys, Arg, Gly, $NH_2$ or is absent;
$Xaa_{46}$ is: His, Ser, Arg, Lys, Pro, Gly, $NH_2$ or is absent; and
$Xaa_{47}$ is: His, Ser, Arg, Lys, $NH_2$ or is absent;
$Xaa_{48}$ is: Gly, His, $NH_2$ or is absent;
$Xaa_{49}$ is: Pro, His, $NH_2$ or is absent; and
$Xaa_{50}$ is: Ser, His, Ser-$NH_2$, His-$NH_2$ or, is absent;

wherein said GLP-1 peptide comprises from one to six further substitutions and provided that if $Xaa_{42}$, $Xaa_{43}$, $Xaa_{44}$, $Xaa_{45}$, $Xaa_{46}$, $Xaa_{47}$, $Xaa_{48}$, or $Xaa_{49}$ is absent each amino acid downstream is absent Additional embodiments of formula 1, formula 2, formula 3, formula 4, and formula 5 include GLP-1 peptides that have valine or glycine at position 8 and glutamic acid at position 22.

The present invention also encompasses a method of stimulating the GLP-1 receptor in a subject in need of such stimulation, said method comprising the step of administering to the subject an effective amount of the GLP-1 peptides described herein. Subjects in need of GLP-1 receptor stimulation include those with non-insulin dependent diabetes, stress-induced hyperglycemia, and obesity.

The GLP-1 peptides of the present invention have various amino acid changes relative to the native GLP-1 molecules and have additional amino acids added to the C-terminus beginning at position 37.

Native GLP-1(7-37)OH has the amino acid sequence of SEQ ID NO: 5:

(SEQ ID NO: 5)
$^7$His-Ala-Glu-$^{10}$Gly-Thr-Phe-Thr-Ser-$^{15}$Asp-Val-Ser-

Ser-Tyr-$^{20}$Leu-Glu-Gly-Gln-Ala-$^{25}$Ala-Lys-Glu-Phe-

Ile-$^{30}$Ala-Trp-Leu-Val-Lys-$^{35}$Gly-Arg-$^{37}$Gly

The native molecule is also amidated in vivo such that the glycine residue at position 37 is replaced with an amide group. By custom in the art, the amino terminus of GLP-1(7-37)OH has been assigned residue number 7 and the carboxyterminus, number 37. The other amino acids in the polypeptide are numbered consecutively, as shown in SEQ ID NO: 4. For example, position 12 is phenylalanine and position 22 is glycine. The same numbering system is used for the extended GLP-1 peptides of the present invention.

The GLP-1 peptides encompassed by the present invention are "extended GLP-1 peptides." Extended GLP-1 peptides have various amino acid substitutions relative to the native GLP-1(7-37) or GLP-1(7-36) molecule and have additional amino acids extending from the C-terminus.

The extended GLP-1 peptides of the present invention have one or more changes selected from the following positions relative to GLP-1(7-37): 7, 8, 12, 16, 18, 19, 20, 22, 25, 27, 30, 33, 34, 36, and 37. In addition, these GLP-1 peptides have at least 4 amino acids added after amino acid residue number 37 ($Xaa_{38}$ through $Xaa_{41}$). Preferably, at least 6 amino acids are added to the C-terminus. Most preferably between 6 and 10 amino acids are added to the C-terminus. Even more preferably, between 7 and 9 amino acids are added to the C-terminus.

The present invention encompasses extended GLP-1 peptides comprising any combination of the amino acids provided in formula 1 (SEQ ID NO:1), formula 2 (SEQ ID NO:2), formula 3 (SEQ ID NO:3), and formula 4 (SEQ ID NO:4) wherein these extended GLP-1 peptides exhibit "insulinotropic activity." Insulinotropic activity refers to the ability to stimulate insulin secretion in response to elevated glucose levels, thereby causing glucose uptake by cells and decreased plasma glucose levels. Insulinotropic activity can be assessed by methods known in the art, including using in vivo experiments and in vitro assays that measure GLP-1 receptor binding activity or receptor activation, e.g., assays employing pancreatic islet cells or insulirioma cells, as described in EP 619,322 to Gelfand, et al., and U.S. Pat. No. 5,120,712, respectively. Insulinotropic activity is routinely measured in humans by measuring insulin levels or C-peptide levels.

For the purposes of the present invention an in vitro GLP-1 receptor signaling assay is used to determine whether a particular extended GLP-1 peptide will exhibit insulinotropic activity in vivo. Extended GLP-1 peptides encompassed by the present invention have an in vitro potency that is not less than $\frac{1}{10}$ the in vitro potency of the DPP-IV resistant GLP-1 analog known as $Val^8$-GLP-1(7-37)OH. More preferably, the extended GLP-1 peptides of the present invention are as potent or more potent than $Val^8$-GLP-1(7-37)OH.

"In vitro potency" as used herein is the measure of the ability of a peptide to activate the GLP-1 receptor in a cell-based assay. In vitro potency is expressed as the "$EC_{50}$" which is the effective concentration of compound that results in 50% activity in a single dose-response experiment. For the purposes of the present invention, in vitro potency is determined using a fluorescence assay that employs HEK-293 Aurora CRE-BLAM cells that stably express the human GLP-1 receptor. These HEK-293 cells have stably integrated a DNA vector having a cAMP response element (CRE) driving expression of the β-lactamase (BLAM) gene. The interaction of a GLP-1 agonist with the receptor initiates a signal that results in activation of the cAMP response element and subsequent expression of β-lactamase. The β-lactamase CCF2/AM substrate that emits fluorescence when it is cleaved by β-lactamase (Aurora Biosciences Corp.) can then be added to cells that have been exposed to a specific amount of GLP-1 agonist to provide a measure of GLP-1 agonist potency. The assay is further described in Zlokarnik et al. (1998) Science 279:84-88 (See also Example 1). The $EC_{50}$ values for the compounds listed in example 1 were determined using the BLAM assay described above by generating a dose response curve using dilutions ranging from 0.00003 nanomolar to 30 nanomolar. Relative in vitro potency values are established by running $Val^8$-GLP-1(7-37)OH as a control and assigning the control a reference value of 1.

Preferably, the extended GLP-1 peptides of the present invention have the amino acid sequence of GLP-1(7-37) modified so that one, two, three, four, five, or six amino acids differ from the amino acid in the corresponding position of GLP-1(7-37) and in addition have at least 4, preferably 6, even more preferably between 6 and 10 amino acids added to the C-terminus.

Preferably, the GLP-1 peptides of the present invention comprise extended GLP-1 analogs wherein the backbone for such analogs or fragments contains an amino acid other than alanine at position 8 (position 8 analogs). The backbone may also include L-histidine, D-histidine, or modified forms of histidine such as desamino-histidine, 2-amino-histidine, β-hydroxy-histidine, homohistidine, α-fluoromethyl-histidine, or α-methyl-histidine at position 7. It is preferable that these position 8 analogs contain one or more additional changes at positions 12, 16, 18, 19, 20, 22, 25, 27, 30, 33, 34, 36, and 37 compared to the corresponding amino acid of native GLP-1(7-37). It is more preferable that these position 8 analogs contain one or more additional changes at positions 16, 18, 22, 25 and 33 compared to the corresponding amino acid of native GLP-1(7-37).

In a preferred embodiment, the amino acid at position 12 of an extended GLP-1 peptide is selected from the group consisting of tryptophan or tyrosine. It is more preferred that in addition to the substitution at position 12, the amino acid at position 8 is substituted with glycine, valine, leucine, isoleucine, serine, threonine, or methionine and more preferably valine or glycine. It is even more preferred that in addition to the substitutions at position 12 and 8, the amino acid at position 22 is substituted with glutamic acid.

In another preferred embodiment, the amino acid at position 16 of an extended GLP-1 peptide is selected from the group consisting of tryptophan, isoleucine, leucine, phenylalanine, or tyrosine. It is preferred that the amino acid at position 16 is tryptophan. It is more preferred that in addition to the substitutions at position 16, the amino acid at position 8 is substituted with glycine, valine, leucine, isoleucine, serine, threonine, or methionine and more preferably valine or glycine. It is even more preferred that in addition to the substitutions at position 16 and 8, the amino acid at position 22 is substituted with glutamic acid. It is also preferred that in addition to the substitutions at positions 16 and 8, the amino acid at position 33 is substituted with isoluecine. It is also preferred that in addition to the substitutions at position 8, 16, and 22, the amino acid at position 36 is substituted with glycine and the amino acid at position 37 is substituted with proline In another preferred embodiment, the amino acid at position 18 of an extended GLP-1 peptide is selected from the group consisting of tryptophan, tyrosine, phenylalanine, lysine, leucine, or isoleucine, preferably tryptophan, tyrosine, and isoleucine. It is more preferred that in addition to the substitution at position 18, the amino acid at position 8 is substituted with glycine, valine, leucine, isoleucine, serine, threonine, or methionine and more preferably valine or glycine. It is even more preferred that in addition to the substitutions at position 18 and 8, the amino acid at position 22 is substituted with glutamic acid. It is also preferred that in addition to the substitutions at positions 18 and 8, the amino acid at position 33 is substituted with isoleucine. It is also preferred that in addition to the substitutions at position 8, 18, and 22, the amino acid at position 36 is substituted with glycine and the amino acid at position 37 is substituted with proline.

In another preferred embodiment, the amino acid at position 19 of an extended GLP-1 peptide is selected from the group consisting of tryptophan or phenylalanine, preferably tryptophan. It is more preferred that in addition to the substitution at position 19, the amino acid at position 8 is substituted with glycine, valine, leucine, isoleucine, serine, threonine, or methionine and more preferably valine or glycine. It is even more preferred that in addition to the substitutions at position 19 and 8, the amino acid at position 22 is substituted with glutamic acid. It is also preferred that in addition to the substitutions at position 8, 19, and 22, the amino acid at position 36 is substituted with glycine and the amino acid at position 37 is substituted with proline.

In another preferred embodiment, the amino acid at position 20 of an extended GLP-1 peptide is selected from the group consisting of phenylalanine, tyrosine, or tryptophan, preferably tryptophan. It is more preferred that in addition to the substitution at position 20, the amino acid at position 8 is substituted with glycine, valine, leucine, isoleucine, serine, threonine, or methionine and more preferably valine or glycine. It is even more preferred that in addition to the substitutions at position 20 and 8, the amino acid at position 22 is substituted with glutamic acid. It is also preferred that in addition to the substitutions at position 8, 20, and 22, the amino acid at position 36 is substituted with glycine and the amino acid at position 37 is substituted with proline.

In another preferred embodiment, the amino acid at position 25 of an extended GLP-1 peptide is selected from the group consisting of valine, isoleucine, and leucine, preferably valine. It is more preferred that in addition to the substitution at position 25, the amino acid at position 8 is substituted with glycine, valine, leucine, isoleucine, serine, threonine, or methionine and more preferably valine or glycine. It is even more preferred that in addition to the substitutions at position 25 and 8, the amino acid at position 22 is substituted with glutamic acid. It is also preferred that in addition to the substitutions at position 8, 22, and 25, the amino acid at position 36 is substituted with glycine and the amino acid at position 37 is substituted with proline.

In another preferred embodiment, the amino acid at position 27 of an extended GLP-1 peptide is selected from the group consisting of isoleucine or alanine. It is more preferred that in addition to the substitution at position 27, the amino acid at position 8 is substituted with glycine, valine, leucine, isoleucine, serine, threonine, or methionine and more preferably valine or glycine. It is even more preferred that in addition to the substitutions at position 27 and 8, the amino acid at position 22 is substituted with glutamic acid. It is also preferred that in addition to the substitutions at position 8, 22, and 27, the amino acid at position 36 is substituted with glycine and the amino acid at position 37 is substituted with proline.

In another preferred embodiment, the amino acid at position 33 of an extended GLP-1 peptide is isoleucine. It is more preferred that in addition to the substitution at position 33, the amino acid at position 8 is substituted with glycine, valine, leucine, isoleucine, serine, threonine, or methionine and more preferably valine or glycine. It is even more preferred that in addition to the substitutions at position 33 and 8, the amino acid at position 22 is substituted with glutamic acid. It is also preferred that in addition to the substitutions at position 8, 22, and 33 the amino acid at position 36 is substituted with glycine and the amino acid at position 37 is substituted with proline.

In another preferred embodiment, the amino acid at position 34 is aspartic acid. It is more preferred that in addition to the substitution at position 34, the amino acid at position 8 is substituted with glycine, valine, leucine, isoleucine, serine, threonine, or methionine and more preferably valine or glycine. It is even more preferred that in addition to the substitutions at position 34 and 8, the amino acid at position 22 is substituted with glutamic acid. It is also preferred that in addition to the substitutions at position 8, 22, and 34 the amino acid at position 36 is substituted with glycine and the amino acid at position 37 is substituted with proline.

The C-terminal extension portion fused to the GLP-1 analog backbones discussed above is at least 4 amino acids in length, preferably between 6 and 10 amino acids in length. Preferably, the extended GLP-1 peptides of the present invention have a serine, proline, or histidine at position 38; a serine, arginine, threonine, tryptophan, or lysine at position 39; a serine or glycine at position 40; an alanine, aspartic acid, arginine, glutamic acid, lysine or glycine at position 41; a proline or alanine at position 42; and a proline or alanine at position 43. Additional amino acids that may be added include a proline, serine, alanine, arginine, lysine, or histidine at position 44; a serine, histidine, proline, lysine or arginine at position 45; a histidine, serine, arginine, or lysine at position 46; and a histidine, serine, arginine, or lysine at position 47. Preferably, histidine is the C-terminal amino acid at either position 42, 43, 44, 45, 46, or 47. Additional amino acids that may be added to the C-terminus also include those specified in formula 1 (SEQ ID NO:1).

It is preferred that when $Xaa_{34}$ is aspartic acid, then $Xaa_{41}$ is arginine or lysine. It is also preferred that $Xaa_{39}$ is serine. It is also preferred that when $Xaa_{41}$ is aspartic acid or arginine, then $Xaa_{42}$, $Xaa_{43}$, and $Xaa_{44}$ are all proline. The C-terminal amino acid may be in the typical acid form or may be amidated.

A preferred genus of extended GLP-1 peptides comprise the amino acid sequence of formula 4 (SEQ ID NO:4)

(SEQ ID NO: 4)
$Xaa_7$-$Xaa_8$-Glu-Gly-Thr-Phe-Thr-Ser-Asp-Val-Ser-Ser-

Tyr-Lys-Glu-$Xaa_{22}$-Gln-Ala-$Xaa_{25}$-Lys-Glu-Phe-Ile-

Ala-Trp-Leu-$Xaa_{33}$-Lys-Gly-Gly-Pro-$Xaa_{38}$-$Xaa_{39}$-

$Xaa_{40}$-$Xaa_{41}$-$Xaa_{42}$-$Xaa_{43}$-$Xaa_{44}$-$Xaa_{45}$-$Xaa_{46}$-$Xaa_{47}$

Formula 4 wherein:
$Xaa_7$ is: L-histidine, D-histidine, desamino-histidine, 2-amino-histidine, β-hydroxy-histidine, homohistidine, α-fluoromethyl-histidine, or α-methyl-histidine;
$Xaa_8$ is: Gly, Val, Leu, Ile, Ser, or Thr;
$Xaa_{22}$ is: Gly, Glu, Asp, or Lys;
$Xaa_{25}$ is: Ala, Val, Ile, or Leu;
$Xaa_{33}$ is: Val or Ile;
$Xaa_{38}$ is: Ser, Pro, or His;
$Xaa_{39}$ is: Ser, Arg, Thr, Trp, or Lys;
$Xaa_{40}$ is: Ser or Gly;
$Xaa_{41}$ is: Ala, Asp, Arg, Glu, Lys, or Gly;
$Xaa_{42}$ is: Pro or Ala;
$Xaa_{43}$ is: Pro or Ala;
$Xaa_{44}$ is: Pro, Ala, Arg, Lys, His, $NH_2$, or is absent;
$Xaa_{45}$ is: Ser, His, Pro, Lys, Arg, $NH_2$ or is absent;
$Xaa_{46}$ is: His, Ser, Arg, Lys, $NH_2$ or is absent; and
$Xaa_{47}$ is: His, Ser, Arg, Lys, $NH_2$ or is absent;

provided that if $Xaa_{44}$, $Xaa_{45}$, $Xaa_{46}$, or $Xaa_{47}$ is absent each amino acid downstream is absent.

Preferred extended GLP-1 peptides are peptides of formula 4 (SEQ ID NO:4) wherein $Xaa_7$ is L-His, $Xaa_8$ is Gly or Val, $Xaa_{22}$ is Glu, $Xaa_{25}$ is Val, $Xaa_{33}$ is Ile, $Xaa_{38}$ is Ser, $Xaa_{39}$ is Ser, $Xaa_{40}$ is Gly, $Xaa_{41}$ is Ala, $Xaa_{42}$ is Pro, $Xaa_{43}$ is Pro, $Xaa_{44}$ is Pro, $Xaa_{45}$ is Ser and $Xaa_{46}$ and $Xaa_{47}$ are absent and amidated forms of thereof. Preferred extended GLP-1 peptides also include peptides of formula 4 (SEQ ID NO:4) wherein $Xaa_7$ is L-His, $Xaa_8$ is Val, $Xaa_{22}$ is Glu, $Xaa_{25}$ is Ala, $Xaa_{33}$ is Ile, $Xaa_{38}$ is Ser, $Xaa_{39}$ is Ser, $Xaa_{40}$ is Gly, $Xaa_{41}$ is Ala, $Xaa_{42}$ is Pro, $Xaa_{43}$ is Pro, $Xaa_{44}$ is Pro, $Xaa_{45}$ is Ser and $Xaa_{46}$ and $Xaa_{47}$ are absent and amidated forms thereof. Other preferred extended GLP-1 peptides include peptides of formula 4 (SEQ ID NO:4) wherein $Xaa_7$ is L-His, $Xaa_8$ is Val, $Xaa_{22}$ is Gly, $Xaa_{25}$ is Ala, $Xaa_{33}$ is Ile, $Xaa_{38}$ is Ser, $Xaa_{39}$ is Ser, $Xaa_{40}$ is Gly, $Xaa_{41}$ is Ala, $Xaa_{42}$ is Pro, $Xaa_{43}$ is Pro, $Xaa_{44}$ is Pro, $Xaa_{45}$ is Ser, and $Xaa_{46}$ and $Xaa_{47}$ are absent and amidated forms thereof.

The present invention encompasses the discovery that specific amino acids added to the C-terminus of a GLP-1 peptide provide specific structural features that protect the peptide from degradation by various proteases yet do not negatively impact the biological activity of the peptide. Further, many of the extended peptides disclosed herein are more potent than DPP-IV resistant GLP-1 analogs such as $Val^8$-GLP-1(7-37) OH.

Example 1 provides in vitro potency data for a representative number of extended GLP-1 peptides. The in vitro potency of the tested extended GLP-1 peptides ranged from about the same as $Val^8$-GLP-1(7-37)OH to greater than 7-fold more potent than $Val^8$-GLP-1(7-37)OH. Further, example 5 illustrates that extended GLP-1 peptides are also more potent in vivo.

Example 2 provides a measure of protease insensitivity for a representative number of extended GLP-1 analogs. The relative proteolytic stability was determined by exposing extended GLP-1 peptides and $Val^8$-GLP-1(7-37)OH to α-chymotrypsin and then plotting the progress of the enzymatic reaction as described in Example 2. The extended GLP-1 peptides tested ranged from as stable as $Val^8$-GLP-1 (7-37)OH to 5-fold more stable than $Val^8$-GLP-1(7-37)OH.

The extended GLP-1 peptides of the present invention also have an increased half-life in vivo as indicated in example 4. The in vivo half-life of these extended peptides is generally longer than the half-life of DPP-IV protected GLP-1 analogs such as $Val^8$-GLP-1(7-37)OH.

The extended GLP-1 peptides of the present invention are suited for oral administration, nasal administration, pulmonary inhalation or parenteral administration. Parenteral administration can include, for example, systemic administration, such as by intramuscular, intravenous, subcutaneous, or intraperitoneal injection. The GLP-1 compounds can be administered to the subject in conjunction with an acceptable pharmaceutical carrier, diluent or excipient as part of a pharmaceutical composition for treating various diseases and conditions discussed herein. The pharmaceutical composition can be a solution or a suspension. Suitable pharmaceutical carriers may contain inert ingredients which do not interact with the peptide or peptide derivative. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Some examples of suitable excipients include lactose, dextrose, sucrose, trehalose, sorbitol, and mannitol.

The GLP-1 compounds may be formulated for administration such that blood plasma levels are maintained in the efficacious range for extended time periods. For example, depot formulations wherein a bioadsorbable polymer is used to provide sustained release over time are also suitable for use in the present invention.

The main barrier to effective oral peptide drug delivery is poor bioavailability due to degradation of peptides by acids and enzymes, poor absorption through epithelial membranes, and transition of peptides to an insoluble form after exposure to the acidic pH environment in the digestive tract. This reduced bioavailability necessitates the use of GLP-1 compounds with increased potency, increased stability, or both. Oral delivery systems for peptides such as those encompassed by the present invention are known in the art. For example, GLP-1 compounds can be encapsulated using microspheres or other carriers and then delivered orally.

The extended GLP-1 peptides described herein can be used to treat subjects with a wide variety of diseases and conditions. The extended GLP-1 peptides encompassed by the present invention exert their biological effects by acting at a receptor referred to as the "GLP-1 receptor" (see Dillon, J. S. et al. (1993), *Endocrinology*, 133: 1907-1910). Subjects with diseases and/or conditions that respond favorably to GLP-1 receptor stimulation or to the administration of extended GLP-1 peptides can therefore be treated. These subjects are said to "be in need of treatment with extended GLP-1 peptides" or "in need of GLP-1 receptor stimulation".

Included are subjects with non-insulin dependent diabetes, insulin dependent diabetes, stress-induced hyperglycemia, stroke (see WO 00/16797 by Efendic), myocardial infarction (see WO 98/08531 by Efendic), catabolic changes after surgery (see U.S. Pat. No. 6,006,753 to Efendic), functional dyspepsia and irritable bowel syndrome (see WO 99/64060 by Efendic). Also included are subjects requiring prophylactic treatment with a GLP-1 peptide, e.g., subjects at risk for developing non-insulin dependent diabetes (see WO 00/07617). Additional subjects include those with impaired glucose tolerance or impaired fasting glucose, subjects with a partial pancreatectomy, subjects having one or more parents with non-insulin dependent diabetes, subjects who have had gestational diabetes and subjects who have had acute or chronic pancreatitis and are at risk for developing non-insulin dependent diabetes.

The extended GLP-1 peptides of the present invention are also useful in treating subjects who are overweight. Particularly suited are those subjects whose body weight is about 25% above normal body weight for the subject's height and body build. Thus, the extended GLP-1 peptides can also be used to treat obesity (see WO 98/19698 by Efendic).

The extended GLP-1 peptides of the present invention can be used to normalize blood glucose levels, prevent pancreatic β-cell deterioration, induce β-cell proliferation, stimulate insulin gene transcription, up-regulate IDX-1/PDX-1 or other growth factors, improve β-cell function, activate dormant β-cells, differentiate cells into β-cells, stimulate β-cell replication, inhibit β-cell apoptosis, regulate body weight, and induce weight loss.

An "effective amount" of an extended GLP-1 peptide is the quantity which results in a desired therapeutic and/or prophylactic effect without causing unacceptable side-effects when administered to a subject in need of GLP-1 receptor stimulation. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of an extended GLP-1 peptide for the treatment of type 2 diabetes is the quantity that would result in greater control of blood glucose concentration than in the absence of treatment, thereby resulting in a delay in the onset of diabetic complications such as retinopathy, neuropathy or kidney disease. An "effective amount" of an extended GLP-1 peptide for the prevention of diabetes is the quantity that would delay, compared with the absence of treatment, the onset of elevated blood glucose levels that require treatment with drugs such as sulfonylureas, thiazolidinediones, insulin and/or bisguanidines.

A typical dose range for the extended GLP-1 peptides of the present invention will range from about 1 µg to about 100 mg per day. Preferably, the dose range is about 5 µg to about 1 mg per day. Even more preferably the dose is about 10 µg to about 100 µg per day.

A "subject" is a mammal, preferably a human, but can also be an animal, e.g., companion animals (e.g., dogs, cats, and the like), farm animals (e.g., cows, sheep, pigs, horses, and the like) and laboratory animals (e.g., rats, mice, guinea pigs, and the like).

The extended GLP-1 peptides of the present invention can be prepared using recombinant DNA technology or by using standard methods of solid-phase peptide synthesis techniques. Peptide synthesizers are commercially available from, for example, Applied Biosystems in Foster City Calif. Reagents for solid phase synthesis are commercially available, for example, from Midwest Biotech (Fishers, Ind.). Solid phase peptide synthesizers can be used according to manufacturers instructions for blocking interfering groups, protecting the amino acid to be reacted, coupling, decoupling, and capping of unreacted amino acids.

Typically, an α-N-carbamoyl protected amino acid and the N-terminal amino acid on the growing peptide chain on a resin is coupled at room temperature in an inert solvent such as dimethylformamide, N-methylpyrrolidone or methylene chloride in the presence of coupling agents such as dicyclohexylcarbodiimide and 1-hydroxybenzotriazole and a base such as diisopropylethylamine. The α-N-carbamoyl protecting group is removed from the resulting peptide resin using a reagent such as trifluoroacetic acid or piperidine, and the coupling reaction repeated with the next desired N-protected amino acid to be added to the peptide chain. Suitable amine protecting groups are well known in the art and are described, for example, in Green and Wuts, "*Protecting Groups in Organic Synthesis*", John Wiley and Sons, 1991, the entire teachings of which are incorporated by reference. Examples include t-butyloxycarbonyl (tBoc) and fluorenylmethoxycarbonyl (Fmoc).

After completion of synthesis, peptides are cleaved from the solid-phase support with simultaneous side-chain deprotection using standard hydrogen fluoride or trifluoroacetic acid cleavage protocols. Crude peptides are then further purified using Reversed-Phase Chromatography on Vydac C18 columns employing linear water-acetonitrile gradients with all solvents containing 0.1% trifluoroacetic acid (TFA). To remove acetonitrile, peptides are lyophilized from a solution containing 0.1% TFA, acetonitrile and water. Purity can be verified by analytical reversed phase chromatography. Identity of peptides can be verified by mass spectrometry. Peptides can be solubilized in aqueous buffers at neutral pH.

EXAMPLES

Example 1

In Vitro Potency:

HEK-293 Aurora CRE-BLAM cells expressing the human GLP-1 receptor are seeded at 20,000 to 40,000 cells/well/100 µl into a 96 well black clear bottom plate. The day after seeding, the medium is replaced with plasma free medium. On the third day after seeding, 20 µl of plasma free medium containing different concentrations of GLP-1 agonist is added to each well to generate a dose response curve. Generally, fourteen dilutions containing from 3 nanomolar to 30 nanomolar GLP-1 compound were used to generate a dose response curve from which $EC_{50}$ values could be determined. After 5 hours of incubation with GLP-1 compound, 20 µl of β-lactamase substrate (CCF2-AM—Aurora Biosciences—product code 100012) was added and incubation was continued for 1 hour at which point the fluorescence was determined on a cytofluor. The following GLP-1 peptides were tested and had $EC_{50}$ values ranging from about the same as to approxi mately 8-fold greater than the activity of Val⁸-GLP-1(7-37) OH:

```
                                            SEQ ID NO: 6
HVEGTFTSDVSSYLEEQAAKEFIAWLVKGRG

SEQ ID NO: 7
HVEGTFTSDVSSYLEEQAAKEFIAWLIDGGPSSGRPPPS-NH2

SEQ ID NO: 8
HVEGTFTSDVSSYLEEQAAKEFIAWLVKGRGSSGDPPPS-NH2

SEQ ID NO: 9
HVEGTFTSDVSSYLEEQAAKEFIAWLVKGRPSSGDPPPS-NH2

SEQ ID NO: 10
HVEGTFTSDVSSYLEEQAAKEFIAWLIKGGPSSGDPPPS-NH2

SEQ ID NO: 11
HVEGTFTSDVSSYLEEQAAKEFIAWLVKGRPSSGAPPPS-NH2

SEQ ID NO: 12
HVEGTFTSDVSSYLEEQAAKEFIAWLIKGGPSSGAPPPS-NH2

SEQ ID NO: 13
HVEGTFTSDVSSYLEEQAVKEFIAWLIKGGPSSGAPPPS-NH2

SEQ ID NO: 14
HVEGTFTSDVSSYLEEQAVKEFIAWLVKGGPSSGAPPPS-NH2

SEQ ID NO: 15
HVEGTFTSDVSSYLEEQAVKEFIAWLIKGGPSSGDPPPS-NH2

SEQ ID NO: 16
HVEGTFTSDVSSYLEEQAAKEFIAWLIKGGGSSGDPPPS-NH2

SEQ ID NO: 17
HVEGTFTSDVSSYLEEQAAKEFIAWLIKGPGSSGDPPPS-NH2

SEQ ID NO: 18
HVEGTFTSDVSSYLEEQAAKEFIAWLIKGGSPSGDPPPS-NH2

SEQ ID NO: 19
HVEGTFTSDVSSYLEEQAAKEFIAWLIKGGPSSGDPPS-NH2

SEQ ID NO: 20
HVEGTFTSDVSSYLEEQAAKEFIAWLIKGGPSSGDPPPS

SEQ ID NO: 21
HVEGTFTSDVSSYLEEQAAKEFIAWLIKGGPSSGDAPPS-NH2

SEQ ID NO: 22
HVEGTFTSDVSSYLEEQAAKEFIAWLIKGGPSSGDPAPS-NH2

SEQ ID NO: 23
HVEGTFTSDVSSYLEEQAAKEFIAWLIKGGPSSGDPPAS-NH2

SEQ ID NO: 24
HVEGTFTSDVSSYLEEQAAKEFIAWLIKGGPSSGDAAAS-NH2

SEQ ID NO: 25
HVEGTFTSDWSSYLEGQAAKEFIAWLIKGGPSSGAPPPS

SEQ ID NO: 26
HVEGTFTSDWSSYLEGQAAKEFIAWLIKGGPSSGAPPPH

SEQ ID NO: 27
HVEGTFTSDVSSYLEGQAAKEFIAWLIKGGPSSGAPPPS

SEQ ID NO: 28
HVEGTFTSDVSSYLEGQAAKEFIAWLIKGGPSSGDPPPS

SEQ ID NO: 29
HVEGTFTSDWSSYLEGQAAKEFIAWLIKGGPSSGAPPPSH

SEQ ID NO: 30
HVEGTFTSDWSSYLEGQAAKEFIAWLIKGGPHSSGAPPPS

SEQ ID NO: 31
HVEGTFTSDVSSYLEGQAAKEFIAWLVKGRGSSGAPPPS

SEQ ID NO: 32
HVEGTFTSDVSSYLEGQAAKEFIAWLVKGGPSSGAPPPS

SEQ ID NO: 33
HVEGTFTSDVSSYLEEQAAKEFIAWLVKGGPSSGAPPPS

SEQ ID NO: 34
HVEGTFTSDVSSYLEEQAAKEFIAWLVKGRGSSGAPPPS

SEQ ID NO: 35
HVEGTFTSDVSSYLEEQAVKEFIAWLIKGRGSSGAPPPS

SEQ ID NO: 36
HVEGTFTSDWSSYLEEQAAKEFIAWLIKGRGSSGAPPPS

SEQ ID NO: 37
HVEGTFTSDVSSYLEEQAAKEFIAWLIKGRGHSSGAPPPS

SEQ ID NO: 38
HVEGTFTSDVSSYLEEQAAKEFIAWLVKGRGHSSGAPPPS

SEQ ID NO: 39
HVEGTFTSDWSSYLEEQAAKEFIAWLIKGGPHSSGAPPPSH

SEQ ID NO: 40
HVEGTFTSDWSSYLEEQAAKEFIAWLIKGGPSSGAPPPSH

SEQ ID NO: 41
HVEGTFTSDVSWYLEGQAVKEFIAWLIKGGPHSSGAPPPS

SEQ ID NO: 42
HVEGTFTSDVSSYLEEQAVKEFIAWLIKGGPSSGAPPPS

SEQ ID NO: 43
HVEGTFTSDVSSYLEEQAVKEFIAWLIKGGPSSGAPPPSH

SEQ ID NO: 44
HVEGTFTSDWSSYLEEQAVKEFIAWLIKGGPSSGAPPPS

SEQ ID NO: 45
HVEGTFTSDWSSYLEEQAVKEFIAWLIKGGPSSGAPPPSH

SEQ ID NO: 46
HVEGTFTSDWSSYLEEQAVKEFIAWLIKGGPHSSGAPPPS

SEQ ID NO: 47
HVEGTFTSDWSKYLEEQAVKEFIAWLIKGGPSSGAPPPSH

SEQ ID NO: 48
HVEGTFTSDVSSYLEEQAVKEFIAWLIKGGPSSGAPPPRG

SEQ ID NO: 49
HVEGTFTSDVSSYLEEQAVKEFIAWLIKGGPSSGAPPPRG-NH2

SEQ ID NO: 50
HVEGTFTSDVSSYLEEQAAKEFIAWLVKGGPSSGAPPPS-NH2

SEQ ID NO: 51
HVEGTFTSDVSSYLEEQAAKEFIAWLVDGGPSSGRPPPS-NH2

SEQ ID NO: 52
HVEGTFTSDVSSYLEEQAAKEFIAWLVDGGPSSGRPPPS

SEQ ID NO: 53
HVEGTFTSDVSSYLEEQAAKEFIAWLVDGGPSSGKPPPS

SEQ ID NO: 54
HVEGTFTSDVSSYLEEQAAKEFIAWLVDGGPSSGRG

SEQ ID NO: 55
HVEGTFTSDVSSYLEEQAAKEFIAWLIKGGPSSGAPPPS

SEQ ID NO: 56
HVEGTFTSDVSSYLEEQAAKEFIAWLVKGGPSWGAPPPS

SEQ ID NO: 57
HVEGTFTSDVSSYLEEQAAKEFIAWLIKGGPSSGAPPPGPS

SEQ ID NO: 58
HVEGTFTSDVSSYLEEQAAKEFIAWLIKGGPSSGAPPPGPSGPS
```

Example 2

Proteolytic Stability:

The relative susceptibility of various extended GLP-1 peptides to α-chymotrypsin was assessed in a reaction mixture with the control peptide Val$^8$-GLP-1(7-37)OH. A 10 mM phosphate/citrate solution, pH 7.4, was prepared containing GLP-1 peptides at a concentration of 100 µM. A 10 µl aliquot of this solution was then incubated at 4° C. in a 200 ul 10 mM phosphate/citrate solution, pH 7.4, containing 10 mM CaCl$_2$. Alpha-Chymotrypsin (SIGMA, C-3142 lot 89F8155) was then added to a final concentration of 250 ng/ml. A 20 µl aliquot was injected onto an analytical Zorbax 300SB-C8 (4.6 mm i.d.×50 mm) column at a 1 ml/min flowrate in 10% acetonitrile/0.075% TFA before addition of the enzyme, as well as 20, 40, 60, 80, and 100 minutes following addition of the enzyme. Peaks were separated with a gradient of 10 to 90% acetonitrile/0.075% TFA over 15 min. The progress of the enzymatic reaction was followed by plotting loss of peak area of the starting material over time. The rate of proteolytic degradation was calculated from the initial rate of cleavage (timepoint 0 and 20 min) and directly compared to the rate of cleavage of the control peptide Val$^8$-GLP-1(7-37)OH. The following extended GLP-1 peptides were tested and had stability rates ranging from about the same as to greater than 5-fold more stable than Val$^8$-GLP-1(7-37)OH:

```
                                           SEQ ID NO: 10
HVEGTFTSDVSSYLEEQAAKEFIAWLIKGGPSSGDPPPS-NH2

SEQ ID NO: 7
HVEGTFTSDVSSYLEEQAAKEFIAWLIDGGPSSGRPPPS-NH2

SEQ ID NO: 8
HVEGTFTSDVSSYLEEQAAKEFIAWLVKGRGSSGDPPPS-NH2

SEQ ID NO: 9
HVEGTFTSDVSSYLEEQAAKEFIAWLVKGRPSSGDPPPS-NH2

SEQ ID NO: 12
HVEGTFTSDVSSYLEEQAAKEFIAWLIKGGPSSGAPPPS-NH2

SEQ ID NO: 13
HVEGTFTSDVSSYLEEQAVKEFIAWLIKGGPSSGAPPPS-NH2

SEQ ID NO: 14
HVEGTFTSDVSSYLEEQAVKEFIAWLVKGGPSSGAPPPS-NH2

SEQ ID NO: 15
HVEGTFTSDVSSYLEEQAVKEFIAWLIKGGPSSGDPPPS-NH2

SEQ ID NO: 16
HVEGTFTSDVSSYLEEQAAKEFIAWLIKGGGSSGDPPPS-NH2

SEQ ID NO: 17
HVEGTFTSDVSSYLEEQAAKEFIAWLIKGPGSSGDPPPS-NH2

SEQ ID NO: 18
HVEGTFTSDVSSYLEEQAAKEFIAWLIKGGSPSGDPPPS-NH2

SEQ ID NO: 19
HVEGTFTSDVSSYLEEQAAKEFIAWLIKGGPSSGDPPS-NH2

SEQ ID NO: 20
HVEGTFTSDVSSYLEEQAAKEFIAWLIKGGPSSGDPPPS

SEQ ID NO: 21
HVEGTFTSDVSSYLEEQAAKEFIAWLIKGGPSSGDAPS-NH2

SEQ ID NO: 22
HVEGTFTSDVSSYLEEQAAKEFIAWLIKGGPSSGDPAPS-NH2

SEQ ID NO: 23
HVEGTFTSDVSSYLEEQAAKEFIAWLIKGGPSSGDPPAS-NH2

SEQ ID NO: 24
HVEGTFTSDVSSYLEEQAAKEFIAWLIKGGPSSGDAAAS-NH2

SEQ ID NO: 25
HVEGTFTSDWSSYLEGQAAKEFIAWLIKGGPSSGAPPPS

SEQ ID NO: 26
HVEGTFTSDWSSYLEGQAAKEFIAWLIKGGPSSGAPPPH

SEQ ID NO: 27
HVEGTFTSDVSSYLEGQAAKEFIAWLIKGGPSSGAPPPS

SEQ ID NO: 32
HVEGTFTSDVSSYLEGQAAKEFIAWLVKGGPSSGAPPPS

SEQ ID NO: 33
HVEGTFTSDVSSYLEEQAAKEFIAWLVKGGPSSGAPPPS

SEQ ID NO: 38
HVEGTFTSDVSSYLEEQAAKEFIAWLVKGRGHSSGAPPPS

SEQ ID NO: 39
HVEGTFTSDWSSYLEEQAAKEFIAWLIKGGPHSSGAPPPSH

SEQ ID NO: 43
HVEGTFTSDVSSYLEEQAVKEFIAWLIKGGPSSGAPPPSH

SEQ ID NO: 48
HVEGTFTSDVSSYLEEQAVKEFIAWLIKGGPSSGAPPPRG

SEQ ID NO: 54
HVEGTFTSDVSSYLEEQAAKEFIAWLVDGGPSSGRG
```

Example 3

Physical Stability:

Extended GLP-1 peptides were analyzed with respect to their potential to aggregate in solution. In general, peptides in solution were stirred at elevated temperature in a suitable buffer while recording turbidity at 350 nm as a function of time. Time to the onset of aggregation was measured to quantify the potential of a given GLP molecule to aggregate under these stressed conditions.

A GLP-1 peptide was first dissolved under alkaline conditions (pH 10.5) for 30 minutes to dissolve any pre-aggregated material. The solution was then adjusted to pH 7.4 and filtered. Specifically, 4 mg of a lyophilized GLP-1 compound was dissolved in 3 ml of 10 mM phosphate/10 mM citrate. The pH was adjusted to 10.0-10.5 and held for 30 minutes. The solution was adjusted with HCl to pH 7.4 and filtered through a suitable filter, for example a Millex GV syringe filter (Millipore Corporation, Bedford, Mass.). This solution was then diluted to a final sample containing 0.3 mg/mL protein in 10 mM citrate, 10 mM phosphate, 150 mM NaCl, and adjusted to pH 7.4 to 7.5. The sample was incubated at 37° C. in a quartz cuvette. Every five minutes the turbidity of the solution was measured at 350 nm on an AVIV Model 14DS UV-VIS spectrophotometer (Lakewood, N.J.). For 30 seconds prior to and during the measurement the solution was stirred using a magnetic stir bar from Starna Cells, Inc. (Atascadero, Calif.). An increase in OD at 350 nm indicates aggregation of the GLP-peptide. The time to aggregation was approximated by the intersection of linear fits to the pre-growth and growth phase according to the method of Drake (Arvinte T, Cudd A, and Drake A F. (1993) *J. Biol. Chem.* 268, 6415-6422).

The cuvette was cleaned between experiments with a caustic soap solution (e.g., Contrad-70). The following extended GLP-1 peptides were tested and were stable in solution for at least 55 hours compared to Val$^8$-GLP-1(7-37)OH which was stable for about 1 hour:

```
                                         SEQ ID NO: 10
HVEGTFTSDVSSYLEEQAAKEFIAWLIKGGPSSGDPPPS-NH2

SEQ ID NO: 7
HVEGTFTSDVSSYLEEQAAKEFIAWLIDGGPSSGRPPPS-NH2

SEQ ID NO: 8
HVEGTFTSDVSSYLEEQAAKEFIAWLVKGRGSSGDPPPS-NH2

SEQ ID NO: 15
HVEGTFTSDVSSYLEEQAVKEFIAWLIKGGPSSGDPPPS-NH2

SEQ ID NO: 20
HVEGTFTSDVSSYLEEQAAKEFIAWLIKGGPSSGDPPPS

SEQ ID NO: 25
HVEGTFTSDWSSYLEGQAAKEFIAWLIKGGPSSGAPPPS

SEQ ID NO: 26
HVEGTFTSDWSSYLEGQAAKEFIAWLIKGGPSSGAPPPH

SEQ ID NO: 27
HVEGTFTSDVSSYLEGQAAKEFIAWLIKGGPSSGAPPPS

SEQ ID NO: 30
HVEGTFTSDWSSYLEGQAAKEFIAWLIKGGPHSSGAPPPS

SEQ ID NO: 32
HVEGTFTSDVSSYLEGQAAKEFIAWLVKGGPSSGAPPPS

SEQ ID NO: 33
HVEGTFTSDVSSYLEEQAAKEFIAWLVKGGPSSGAPPPS

SEQ ID NO: 42
HVEGTFTSDVSSYLEEQAVKEFIAWLIKGGPSSGAPPPS

SEQ ID NO: 39
HVEGTFTSDWSSYLEEQAAKEFIAWLIKGGPHSSGAPPPSH

SEQ ID NO: 44
HVEGTFTSDWSSYLEEQAVKEFIAWLIKGGPSSGAPPPS

SEQ ID NO: 54
HVEGTFTSDVSSYLEEQAAKEFIAWLVDGGPSSGRG

SEQ ID NO: 55
HVEGTFTSDVSSYLEEQAAKEFIAWLIKGGPSSGAPPPS

SEQ ID NO: 31
HVEGTFTSDVSSYLEGQAAKEFIAWLVKGRGSSGAPPPS

SEQ ID NO: 35
HVEGTFTSDVSSYLEHQAVKEFIAWLIKGRGSSGAPPPS

SEQ ID NO: 36
HVEGTFTSDWSSYLEEQAAKEFIAWLIKGRGSSGAPPPS
```

Example 4

Pharmacokinetics of an Extended GLP-1 Peptide:

Pharmacokinetic parameters were determined for the following 5 different extended GLP-1 peptides:

```
                                         SEQ ID NO:10
Compound 1: HVEGTFTSDVSSYLEEQAAKEFIAWLIKGGPSSGDPPP
S-NH2

SEQ ID NO:20
Compound 2: HVEGTFTSDVSSYLEEQAAKEFIAWLIKGGPSSGDPPP
S

SEQ ID NO:34
Compound 3: HVEGTFTSDVSSYLEEQAAKEFIAWLVKGRGSSGAPPP
S

SEQ ID NO:31
Compound 4: HVEGTFTSDVSSYLEGQAAKEFIAWLVKGRGSSGAPPP
S

SEQ ID NO:36
Compound 5: HVEGTFTSDWSSYLEEQAAKEFIAWLIKGRGSSGAPPP
S
```

Parameters were determined following a single intravenous dose of 10 μg/kg in four different rats. Data are listed in Tables 1 and 2

TABLE 1

PK parameters for extended GLP-1 peptides following a single intravenous injection of 10 μg/kg to Sprague Dawley rats.

| Compound Administered | Subject | Cmax (ng/mL) | AUC$_{0\text{-last}}$ (ng*min/mL) | t½ (min) | Cl (mL/min/kg) | V$_{ss}$ (mL/kg) |
|---|---|---|---|---|---|---|
| 1 | Rat1 | 22.8 | 448.5 | 10.9 | 22.3 | 265.7 |
|   | Rat2 | 22.4 | 469.4 | 10.1 | 21.3 | 270.4 |
|   | Rat3 | 24.6 | 504.8 | 13.1 | 19.8 | 272.7 |
|   | Rat4 | 24.1 | 478.8 | 10.1 | 20.9 | 246.3 |
|   | Mean | 23.5 | 475.4 | 11.0 | 21.1 | 263.8 |
|   | S.D | 1.0 | 23.3 | 1.4 | 41.0 | 12.0 |
| 2 | Rat1 | 9.8 | 512.8 | 35.8 | 19.5 | 973.9 |
|   | Rat2 | 16.9 | 312.2 | 12.3 | 32.0 | 355.7 |
|   | Rat3 | 21.4 | 430.0 | 10.6 | 23.3 | 283.3 |
|   | Rat4 | 21.1 | 409.1 | 14.4 | 24.4 | 313.4 |
|   | Mean | 17.3 | 416.0 | 18.3 | 24.8 | 481.6 |
|   | S.D | 5.4 | 82.4 | 11.8 | 5.3 | 329.6 |
| 3 | Rat1 | 23.6 | 466.8 | 11.6 | 21.4 | 263.3 |
|   | Rat2 | 22.7 | 465.6 | 11.7 | 21.5 | 280.5 |
|   | Rat3 | 24.3 | 492.5 | 12.0 | 20.3 | 262.4 |
|   | Rat4 | 21.1 | 409.1 | 14.4 | 24.4 | 313.4 |
|   | Mean | 23.3 | 477.5 | 12.1 | 21.0 | 277.2 |
|   | S.D. | 0.9 | 13.4 | 0.6 | 0.6 | 18.8 |
| 4 | Rat1 | 25.4 | 560.0 | 12.0 | 17.9 | 258.6 |
|   | Rat2 | 24.9 | 486.7 | 11.9 | 20.5 | 251.1 |
|   | Rat3 | 20.0 | 424.9 | 11.2 | 23.5 | 315.9 |
|   | Rat4 | 24.0 | 461.5 | 11.0 | 21.7 | 249.2 |
|   | Mean | 23.6 | 483.3 | 11.5 | 20.9 | 268.7 |
|   | S.D. | 2.5 | 57.2 | 0.5 | 2.4 | 31.7 |
| 5 | Rat1 | 35.9 | 747.1 | 11.9 | 13.4 | 179.2 |
|   | Rat2 | 25.9 | 525.9 | 11.6 | 19.0 | 243.6 |
|   | Rat3 | 39.7 | 852.0 | 13.2 | 11.7 | 171.6 |
|   | Rat4 | 29.6 | 546.3 | 10.9 | 18.3 | 188.1 |
|   | Mean | 32.8 | 667.9 | 11.9 | 15.6 | 195.6 |
|   | S.D. | 6.2 | 158.2 | 1.0 | 3.6 | 32.7 |

Abbreviations: , kg = killigram, μg = microgram, min = minute, ng = nanogram, mL = milliliter, C$_{max}$ = maximum plasma concentration, AUC = area under the concentration curve, t½ = plasma half life, Cl = clearance, V = volume of distribution based on the terminal phase, SD = Standard Deviation.

TABLE 2

Plasma Concentrations (pg/mL) of extended GLP-1 peptides following a single intravenous administration of 10 μg/kg to Sprague Dawley rats.

| Compound | Rat # | Time (min) | | | | |
|---|---|---|---|---|---|---|
|   |   | 5 | 15 | 30 | 60 | 120 |
| 1 | 1 | 22778 | 8322 | 2894 | 467 | <150 [a] |
|   | 2 | 22369 | 11008 | 3119 | 478 | <150 [a] |
|   | 3 | 24565 | 10027 | 3115 | 857 | <150 [a] |
|   | 4 | 24119 | 9088 | 3279 | 415 | <150 [a] |
|   | Mean | 23458 | 9611 | 3102 | 554 | NC |
|   | SD | 1051 | 1163 | 158 | 204 | NC |
| 2 | 1 | 9827 | 7529 | 4990 | 3073 | 1045 |
|   | 2 | 16926 | 4364 | 1876 | <150 [a] | <150 [a] |
|   | 3 | 21404 | 9191 | 2622 | 459 | <150 [a] |
|   | 4 | 21092 | 6199 | 2318 | 671 | <150 [a] |
|   | Mean | 17312 | 6821 | 2952 | 1051 | NC |
|   | SD | 5392 | 2045 | 1393 | 1377 | NC |
| 3 | 1 | 23585 | 8604 | 2996 | 566 | <150 [a] |
|   | 2 | 22666 | 8467 | 3477 | 589 | <150 [a] |
|   | 3 | 24349 | 9240 | 3282 | 670 | <150 [a] |
|   | 4 | 22377 | 8930 | 4010 | 802 | <150 [a] |

TABLE 2-continued

Plasma Concentrations (pg/mL) of extended GLP-1 peptides following a single intravenous administration of 10 μg/kg to Sprague Dawley rats.

| Compound | Rat # | Time (min) | | | | |
|---|---|---|---|---|---|---|
| | | 5 | 15 | 30 | 60 | 120 |
| | Mean | 23244 | 8810 | 3441 | 657 | NC |
| | SD | 899 | 346 | 428 | 107 | NC |
| 4 | 1 | 25386 | 12141 | 4366 | 869 | <150 [a] |
| | 2 | 24853 | 9246 | 2782 | 631 | <150 [a] |
| | 3 | 20017 | 9576 | 2894 | 564 | <150 [a] |
| | 4 | 23963 | 8475 | 2680 | 480 | <150 [a] |
| | Mean | 23555 | 9860 | 3181 | 636 | NC |
| | SD | 2430 | 1589 | 795 | 167 | NC |
| 5 | 1 | 35938 | 16063 | 4773 | 1089 | <150 [a] |
| | 2 | 25899 | 10678 | 3361 | 686 | <150 [a] |
| | 3 | 39673 | 15595 | 6757 | 1450 | <150 [a] |
| | 4 | 29602 | 8169 | 2991 | 458 | <150 [a] |
| | Mean | 32778 | 12626 | 4471 | 921 | NC |
| | SD | 6190 | 3842 | 1707 | 439 | NC |

NC = not calculated;
μg = microgram;
pg = picogram;
mL = milliliter;
kg = kilogram;
min = minute.
[a] Less than the lower limit of quantitation (a value of zero was used for the purpose of calculations).

Example 5

In Vivo Activity of Extended GLP-1 Peptides:

Several different extended and non-extended GLP-1 peptides were tested for activity in a hyperglycemic clamp study in dogs. Glucose was infused for 200 minutes to maintain constant levels. For the first 80 minutes dogs were infused intravenously with vehicle to establish a baseline insulin concentration. For the next 60 minutes, GLP-1 peptides were administered at a rate of 1 pmol/kg/min. For the final 60 minutes the infusion rate of each GLP-1 compound was increased to 3 pmol/kg/min. Blood samples were taken periodically for the determination of insulin and GLP-1 peptide concentrations. Insulin change values were calculated as the difference between the value at time t and the average value during the last 20 minutes of the control period (60-80) minutes and are presented in Table 3. Areas under the insulin change curves were calculated using the trapezoidal rule over the last 30 minutes of each infusion period. GLP-1 peptide concentrations are presented in Table 4. Values listed are the means±standard error of the mean (SEM).

TABLE 3

Pharmacodynamics from dog hyperglycemic (150 mg/dL) clamp studies

| | | Pharmacodynamics (insulin change AUC; mU·min/mL) Compound Infusion Rate (pmol/kg/min) | |
|---|---|---|---|
| Compound | n | 1 | 3 |
| Vehicle | 5 | 0.4 ± 0.1 | 0.4 ± 0.2 |
| HVEGTFTSDVSSYLEGQAAKEFIAWLVKGRG SEQ ID NO:59 (No Cex) | 5 | 1.1 ± 0.7 | 2.2 ± 1.2 |
| HVEGTFTSDVSSYLEEQAAKEFIAWLIKGGPSSGDPPPS-NH2 SEQ ID NO:10 | 5 | 2.8 ± 1.0 | 5.5 ± 2.1 |
| HVEGTFTSDVSSYLEEQAAKEFIAWLIKGGPSSGDPPPS SEQ ID NO:20 | 5 | 1.5 ± 0.5 | 3.7 ± 1.7 |
| HVEGTFTSDVSSYLEEQAVKEFIAWLIKGGPSSGAPPPS-NH2 SEQ ID NO:13 | 5 | 1.4 ± 0.3 | 4.0 ± 0.9 |
| HVEGTFTSDVSSYLEEQAAKEFIAWLVKGGPSSGAPPPS SEQ ID NO:33 | 5 | 1.9 ± 0.5 | 4.3 ± 1.5 |
| HVEGTFTSDVSSYLEEQAVKEFIAWLIKGRGSSGAPPPS SEQ ID NO:35 | 5 | 1.1 ± 0.1 | 3.7 ± 0.9 |
| HVEGTFTSDVSSYLEEQAVKEFIAWLIKGGPSSGAPPPS SEQ ID NO:42 | 6 | 2.3 ± 0.6 | 6.1 ± 1.5 |
| HVEGTFTSDVSSYLEEQAVKEFIAWLIKGGPSSGAPPPSH SEQ ID NO:43 | 5 | 1.2 ± 0.5 | 4.6 ± 1.9 |
| HVEGTFTSDVSSYLEEQAVKEFIAWLIKGGPSSGAPPPRG SEQ ID NO:48 | 5 | 2.2 ± 0.6 | 4.0 ± 1.4 |
| HVEGTFTSDVSSYLEEQAAKEFIAWLIKGGPSSGAPPPS SEQ ID NO:55 | 7 | 2.2 ± 0.5 | 5.2 ± 1.4 |

TABLE 4

GLP-1 peptide concentration from dog hyperglycemic (150 mg/dL) clamp studies after 60 minutes of compound infusion.

| Compound | n | Compound Concentration (t = 60'; pM) Compound Infusion Rate (pmol/kg/min) | |
|---|---|---|---|
| | | 1 | 3 |
| Vehicle | 5 | — | — |
| HVEGTFTSDVSSYLEGQAAKEFIAWLVKGRG SEQ ID NO:59 (No Cex) | 5 | 166 ± 23 | 410 ± 25 |
| HVEGTFTSDVSSYLEEQAAKEFIAWLIKGGPSSGDPPPS-NH2 SEQ ID NO:10 | 5 | 268 ± 45 | 977 ± 135 |
| HVEGTFTSDVSSYLEEQAAKEFIAWLIKGGPSSGDPPPS SEQ ID NO:20 | 5 | 204 ± 24 | 755 ± 72 |
| HVEGTFTSDVSSYLEEQAVKEFIAWLIKGGPSSGAPPPS-NH2 SEQ ID NO:13 | 5 | 366 ± 59 | 1316 ± 211 |
| HVEGTFTSDVSSYLEEQAVKEFIAWLIKGRGSSGAPPPS SEQ ID NO:35 | 5 | 267 ± 31 | 1036 ± 103 |
| HVEGTFTSDVSSYLEEQAVKEFIAWLIKGGPSSGAPPPS SEQ ID NO:42 | 6 | 276 ± 36 | 1114 ± 139 |
| HVEGTFTSDVSSYLEEQAVKEFIAWLIKGGPSSGAPPPSH SEQ ID NO:43 | 5 | 306 ± 20 | 1057 ± 34 |
| HVEGTFTSDVSSYLEEQAVKEFIAWLIKGGPSSGAPPPRG SEQ ID NO:48 | 5 | 227 ± 40 | 1092 ± 106 |
| HVEGTFTSDVSSYLEEQAAKEFIAWLIKGGPSSGAPPPS SEQ ID NO:55 | 7 | 246 ± 17 | 766 ± 46 |

What is claimed is:

1. An extended GLP-1 peptide comprising an amino acid sequence of the formula:

(SEQ ID NO: 1)
$Xaa_7$-$Xaa_8$-Glu-Gly-Thr-$Xaa_{12}$-Thr-Ser-Asp-$Xaa_{16}$-Ser- $Xaa_{18}$-$Xaa_{19}$-$Xaa_{20}$-Glu-$Xaa_{22}$-Gln-Ala-$Xaa_{25}$-Lys- $Xaa_{27}$-Phe-Ile-$Xaa_{30}$-Trp-Leu-$Xaa_{33}$-$Xaa_{34}$-Gly-$Xaa_{36}$-

$Xaa_{37}$-$Xaa_{38}$-$Xaa_{39}$-$Xaa_{40}$-$Xaa_{41}$-$Xaa_{42}$-$Xaa_{43}$-$Xaa_{44}$-

$Xaa_{45}$-$Xaa_{46}$-$Xaa_{47}$-$Xaa_{48}$-$Xaa_{49}$-$Xaa_{50}$

Formula 1
wherein:
   $Xaa_7$ is: L-histidine;
   $Xaa_8$ is: Gly, or Val;
   $Xaa_{12}$ is: Phe;
   $Xaa_{16}$ is: Val, Trp, Ile, Leu, Phe, or Tyr;
   $Xaa_{18}$ is: Ser;
   $Xaa_{19}$ is: Tyr;
   $Xaa_{20}$ is: Leu, Phe, Tyr, or Trp;
   $Xaa_{22}$ is: Glu;
   $Xaa_{25}$ is: Ala, Val, Ile, or Leu;
   $Xaa_{27}$ is: Glu, Ile, or Ala;
   $Xaa_{30}$ is: Ala or Glu
   $Xaa_{33}$ is: Val or Ile;
   $Xaa_{34}$ is: Lys, Asp, Arg, or Glu;
   $Xaa_{36}$ is: Gly, Pro, or Arg;
   $Xaa_{37}$ is: Gly, Pro, or Ser;
   $Xaa_{38}$ is: Ser, Pro, or His;
   $Xaa_{39}$ is: Ser, Arg, Thr, Trp, or Lys;
   $Xaa_{40}$ is: Ser or Gly;
   $Xaa_{41}$ is: Ala, Asp, Arg, Glu, Lys, or Gly;
   $Xaa_{42}$ is: Pro, or Ala;
   $Xaa_{43}$ is: Pro, or Ala;
   $Xaa_{44}$ is: Pro, Ala, Arg, Lys, or His;
   $Xaa_{45}$ is: Ser, His, Pro, Lys, Arg, or Gly;
   $Xaa_{46}$ is: His, Ser, Arg, Lys, Pro, or Gly;
   $Xaa_{47}$ is: His, Ser, Arg, Lys, $NH_2$ or is absent;
   $Xaa_{48}$ is: Gly, His, $NH_2$ or is absent;
   $Xaa_{49}$ is: Pro, His, $NH_2$ or is absent; and
   $Xaa_{50}$ is: Ser, His, Ser-$NH_2$, His-$NH_2$ or is absent; and
   wherein the first 31 amino acids of the peptide do not differ from GLP-1 (7-37) at more than 6 of the corresponding variable positions and wherein the extended GLP-1 peptide has insulinotropic activity.

2. The GLP-1 peptide of claim 1 wherein the first 31 amino acids of the peptide do not differ from GLP-1(7-37) at more than 5 of the corresponding variable positions.

3. The GLP-1 peptide of claim 2 wherein the first 31 amino acids of the peptide do not differ from GLP-1(7-37) at more than 4 of the corresponding variable positions.

4. The GLP-1 peptide of claim 3 wherein the first 31 amino acids of the peptide do not differ from GLP-1(7-37) at more than 3 of the corresponding variable positions.

5. The GLP-1 peptide of claim 1 wherein $Xaa_{16}$ is Trp.

6. The GLP-1 peptide claim 1 wherein $Xaa_{25}$ is Val.

7. The GLP-1 peptide of claim 1 wherein $Xaa_{33}$ is Ile.

8. The GLP-1 peptide of claim 1 wherein $Xaa_{34}$ is Asp.

9. The GLP-1 peptide of claim 8 wherein $Xaa_{41}$ is Arg.

10. The GLP-1 peptide of claim 1 wherein $Xaa_{36}$ is Gly, and $Xaa_{37}$ is Pro.

11. The GLP-1 peptide of claim 1 wherein $Xaa_{18}$ is Trp.

12. The GLP-1 peptide of claim 1 wherein $Xaa_{20}$ is Trp.

13. The GLP-1 peptide of claim 1 wherein the C-terminal amino acid is amidated.

14. The GLP-1 peptide of claim 1 wherein the C-terminal amino acid is His.

15. A method of stimulating the GLP-1 receptor in a subject in need of blood glucose normalization, said method comprising the step of administering to the subject an effective amount of the GLP-1 peptide of claim 1.

16. The method of claim 15 wherein the subject is being treated for non-insulin dependent diabetes.

* * * * *